United States Patent
Nagore et al.

(10) Patent No.: US 8,679,769 B2
(45) Date of Patent: Mar. 25, 2014

(54) DETECTION OF ENDOMETRIAL SECRETION MARKERS FOR ASSESSMENT OF ENDOMETRIOSIS

(75) Inventors: Daniel Nagore, Derio (ES); Amagoia Ametzazurra, Derio (ES); Antonio Martinez Martinez, Derio (ES); Laureano Simón Buela, Derio (ES)

(73) Assignee: Proteomike, S.L., Derio (ES)

(*) Notice: Subject to any disclaimer, the term of this patent is extended or adjusted under 35 U.S.C. 154(b) by 672 days.

(21) Appl. No.: 12/811,159

(22) PCT Filed: Nov. 26, 2008

(86) PCT No.: PCT/EP2008/010013
§ 371 (c)(1),
(2), (4) Date: Oct. 1, 2010

(87) PCT Pub. No.: WO2009/068254
PCT Pub. Date: Jun. 4, 2009

(65) Prior Publication Data
US 2011/0015087 A1    Jan. 20, 2011

(30) Foreign Application Priority Data
Nov. 28, 2007  (EP) .................................... 07384037

(51) Int. Cl.
*G01N 33/53*    (2006.01)
*G01N 31/00*    (2006.01)

(52) U.S. Cl.
USPC ............. 435/7.21; 435/7.1; 436/86; 436/501; 436/518; 530/300; 530/350

(58) Field of Classification Search
USPC .................... 435/7.1, 7.21; 436/86, 501, 518; 530/300, 350
See application file for complete search history.

(56) References Cited

FOREIGN PATENT DOCUMENTS

| EP | 1321768 A1 | 6/2003 |
|---|---|---|
| WO | 2004024952 A1 | 3/2004 |

OTHER PUBLICATIONS

Eyster, K.M., Ph.D., et al., DNA microarray analysis of gene expression markers of endometriosis, Fertility and Sterility, Jan. 2002, pp. 38-42, vol. 77, No. 1.
Eyster, K.M., Ph.D., et al., Whole genome deoxyribonucleic acid microarray analysis of gene expression in ectopic versus eutopic endometrium, Fertility and Sterility, Dec. 2007, pp. 1505-1533, vol. 88, No. 6.
Lessard, J.L., Two Monoclonal Antibodies to Actin: One Muscle Selective and One Generally Reactive, Cell Motility and the Cytoskeleton, 1988, pp. 349-362, vol. 10.
Zhang, H., M.D., et al., Use of proteomic analysis of endometriosis to identify different protein expression in patients with endometriosis versus normal controls, Fertility and Sterility, Aug. 2006, pp. 274-282, vol. 86, No. 2.
Hur, S. et al.; "Polymorphisms of the genes encoding the GSTM1, GSTT1 and GSTP1 in Korean women: no association with endometriosis," Molecular Human Reproduction, 2007, pp. 15-19, vol. 11.
Koninckx, Phipippe, et al., "CA-125 and placental protein 14 concentrations in plasma and peritoneal fluid of women with deeply infiltrating pelvic endometriosis," Fertility and Sterility, 1992, pp. 523-530.
Telimaa, Sakari, et al., "Elevated serum levels of endometrial secretory protein PP14 in patients with advanced endometriosis," Am J Obstet Gynecol, 1989, pp. 866-871, vol. 161.
Flores, Idhaliz, et al., "Molecular profiling of experimental endometriosis identified gene expression patterns in common with human disease," Fertility and Sterility, 2007, pp. 1180-1199, vol. 87.
Ametzazurra, A., et al.; "Endometrial fluid is a specific and non-invasive biological sample for protein biomarker identification in endometriosis," Human Reproduction, 2009, pp. 954-965, vol. 24.

*Primary Examiner* — Lisa Cook
(74) *Attorney, Agent, or Firm* — Tristan A. Fuierer; Moore & Van Allen, PLLC

(57) ABSTRACT

The present invention refers to a group of biomarkers and to non-invasive in vitro methods for the diagnosis or prognosis of endometriosis, as well as to a kit to perform said methods.

14 Claims, 2 Drawing Sheets

DETECTION OF ENDOMETRIAL SECRETION MARKERS FOR ASSESSMENT OF ENDOMETRIOSIS

CROSS-REFERENCE TO RELATED APPLICATIONS

This application is filed under the provisions of 35 U.S.C. §371 and claims the priority of International Patent Application No. PCT/EP2008/010013 filed on 26 Nov. 2008 entitled "Detection of Endometrial Secretion Markers for Assessment of Endometriosis" in the name of Daniel NAGORE CASAS, et al., which claims priority of European Patent Application No. EP 07384037.3 filed on 28 Nov. 2007, both of which are hereby incorporated by reference herein in their entirety.

FIELD OF THE INVENTION

The present invention refers to a group of biomarkers and to a non-invasive in vitro method for the diagnosis of endometriosis, as well as to the use of peptide sequences derived from selected biomarkers and to a kit to perform the method.

BACKGROUND OF THE INVENTION

Endometriosis is an estrogen dependent gynecologic chronic disease defined as the presence of endometrial stromal or glandular cells outside the uterine cavity (31). Endometriotic lesions are most commonly located in ovaries, the pelvic peritoneum and the uterosacral ligaments, but may appear in almost any part of the body (2). Those lesions can vary from a small number of vesicles sticked to the pelvic peritoneum (minimal or mild stage of the disease) to the presence of endometriotic ovarian cysts, thick pelvic adhesions or profound rectovaginal endometriosis (advanced stage of the disease). Endometriosis severity is classified according to the American Society for Reproductive Medicine classification (ASRM) in four stages: I-Minimal, II-Mild, III-Moderate and IV-Severe.

Endometriosis affects up to 10% of women of fertile age, being the major cause of infertility (the incidence in women with infertility rises to up to 40%). Other common symptoms include dysmenorrhoea (pelvic pain with menstruation), dyspareunia (pain with intercourse) and chronic pelvic pain (51).

Despite the identification of endometriosis in the late 1800s, the etiology and pathogenesis of this disease still remains unclear (23). Several theories have been proposed to explain the pathogenesis of this disease, but the most accepted theory is the one proposed by Sampson about the retrograde menstruation. According to this theory, endometrial cells are refluxed through the fallopian tubes during the menstruation and implant onto peritoneum or pelvic organs. But the retrograde menstruation is a very common phenomenon among women of reproductive age (occurs in 90% of women) and only 10% develop endometriosis, so there must be other factors that may contribute to the pathophysiology and/or pathogenesis of endometriosis. Genetic predisposition, environmental factors, and alterations in immune and endocrine functions are believed to play significant roles in the establishment and maintenance of endometriosis.

Although the eutopic endometriums of women with and without endometriosis are histologically similar, studies revealed that there are many differences between these two tissues. Invasive properties, decreased apoptosis, alterations in expression of specific gene and proteins, and increased steroid and cytokine production have been identified in eutopic endometrium of women with endometriosis (69).

Currently, laparoscopy offers the most specific and sensitive technique for evaluating and monitoring endometriosis. Even so, microscopic or occult endometriosis may be misdiagnosed because of the inability to visualize the lesions (77). Furthermore, it has been described that one-third of all diagnostic laparoscopies reveal endometriosis, one-third reveal no visible pathology, and the remaining one-third demonstrate a variety of other gynecologic conditions. Thus, two-thirds of all patients who undergo this invasive diagnostic procedure will not have endometriosis (17).

Actually, the average delay in the diagnosis of this disease is 9.3 years (18). Attempts for early diagnosis and treatments of endometriosis have been weighed down by lack of proper methods to study and manage the disease. Furthermore, the need for non-invasive diagnostic methods is evident because the laparoscopy is a surgical procedure with potentially dangerous risks, such as vascular or intestinal injury (33).

Therefore, the analysis of differential protein expression, using proteomic approaches, in relation to the disease onset and progression will lead the development of non-invasive method for early diagnosis of endometriosis disease.

SUMMARY OF THE INVENTION

A first aspect of the invention relates to a group of biomarkers for the diagnosis or prognosis of endometriosis comprising the biomarkers ACTG1, SAHH, ADSS, NUDT5, AK1A1, AL1A3, AMY1, ANXA1, APOA1, ACTB, APOH, BPGM, CAT, CLIC4, CCDC94, AMPL, CAPZB, FRIH, FRIL, BLVRB, LEG1, GSTO1, GSTP1, PAEP, LGUL, HSPB1, HBB, LEI, MSN, PPIA, PGAM1, PMVK, PCBP1, PNPO, PSB3, PSD7, PSD10, 1433B, 1433G, 1433S, 1433T, 1433Z, ARHGDIA, GD15, PRPS2, SEP11, NEK7, SAS, TCTP, TBB5 and WDR1 or their transcriptional or post-translational variants, and combinations thereof.

A second aspect of the invention relates to a non-invasive in vitro method comprising a) measuring one or more biomarkers selected from the group of biomarkers as defined in claim 1 in a sample from an individual, and b) comparing the measurements of the one or more biomarkers in the sample with the measurement of the one or more biomarkers in a normal sample, wherein an alteration in the measurement of the one or more biomarkers compared to the measurement of the one or more biomarkers in the normal sample is indicative of endometriosis.

A third aspect of the invention relates to a non-invasive in vitro method comprising a) measuring one or more ratios between the amount of one or more biomarkers selected from the group of biomarkers as defined in claim 1 in a sample from an individual and one or more reference proteins independently selected from the group comprising constantly expressed proteins and differentially expressed proteins in the same sample, and b) comparing the ratios of the one or more biomarkers in the sample relative to the one or more reference proteins, wherein an alteration in the ratio in the sample compared to the ratio in the normal sample is indicative of endometriosis.

Another aspect of the invention relates to a non-invasive in vitro method comprising a) measuring one or more ratios between two or more biomarkers selected from the group of biomarkers as defined in claim 1 in a sample from an individual, and b) comparing the ratios obtained between the two or more biomarkers in the sample with the ratios obtained between the same two or more biomarkers in a normal sample, wherein an alteration in the ratios in the sample compared to the ratios in the normal sample is indicative of endometriosis.

Another aspect of the invention relates to the use of one or more peptide sequences derived from one or more biomarkers selected from the group of biomarkers described above employed to detect the presence of endometriosis and establish the diagnosis (including the stage or severity of the disease), or prognosis of endometriosis and to monitor the effect of the treatment administered to an individual suffering from this disease or to assess the lack of disease after surgical resection.

Another aspect of the invention relates to the use of one or more nucleotide or peptide sequences derived from one or more biomarkers selected from the group of biomarkers described above, in methods to screen for, identify, develop and evaluate the efficiency of compounds to endometriosis.

Another aspect of the invention relates to a kit to perform the method described above comprising any combination of antibodies that specifically recognises one or more biomarkers and a carrier in suitable packaging.

DETAILED DESCRIPTION OF THE INVENTION

Figure 1:
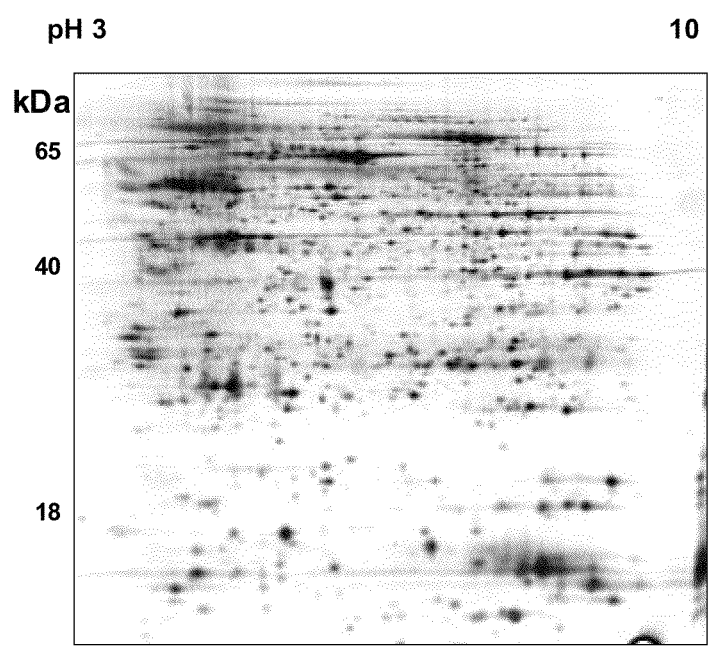
FIG. 1 shows a typical 2D in pH 3-10 gradient image gel obtained from an endometrial aspirate sample. X-axis represents the first dimension, i.e. separation by isoelectric point and Y-axis represents the second dimension (SDS-PAGE), i.e. separation by molecular weight.

The present invention refers to a group comprising 51 biomarkers that are of significant value for the detection, diagnosis, prognosis and/or monitoring of endometriosis: Said biomarkers are as follows:
ACTIN, CYTOPLASMIC 2 (ACTG1) (P63261). This protein, also named DFNA20 or gamma-actin, belongs to the actin family. DFNA20 is a gene causing dominant, nonsyndromic, progressive hearing loss (45) due to missense mutations in highly conserved actin domains, as it has been described that many of the mutations known to cause deafness occur in genes that interact with actin (78). A major factor in the deafness caused by these mutations is an altered ability of the actin filaments to be properly regulated by actin-binding proteins rather than an inability to polymerise (4).
ADENOSYLHOMOCYSTEINASE (SAHH, AHCY) (P23526) is a cytoplasmic protein that belongs to the adenosylhomocysteinase family. Catalizes the breakdown of S-adenosylhomocysteine (AdoHcy) to homocysteine and adenosine (68). It is a competitive inhibitor of S-adenosyl-L-methionine-dependent methyl transferase reactions; therefore it may play a key role in the control of methylations via regulation of the intracellular concentration of adenosylhomocysteine.

Defects in AHOY are a cause of hypermethioninemia, a disease characterized by elevated levels of methionine in the sera.
ADENYLOSUCCINATE SYNTHETASE (ADSS) (P30520), is a cytoplasmic protein that belongs to the adenylosuccinate synthetase family. It plays an important role in the de novo pathway of purine nucleotide biosynthesis. This enzyme is inhibited by a metabolite of alanosine, an aspartic acid analog that is highly cytotoxic for most cells (10). In vertebrates there are two isozymes of this protein, named ADSS1 and ADD2. In pigs it is described that ADSS1 gene is predominantly expressed in the striated muscle tissues, while ADSS2 gene is widely distributed in all the tissues (35).
ADP-SUGAR PYROPHOSPHATASE (NUDT5) (Q9UKK9). Belonging to the Nudix hydrolase family, this protein hydrolyses ADP-ribose, ADP-mannose, and ADP-glucose (76). It also can hydrolyse other nucleotide sugars with lower activity. It is widely expressed, being above all in the liver.

It has recently been described that nitric oxide (NO) stimulates nonenzymatic ADP-ribosylation of NUDT5 using ADP-ribose, and consequently activates its ADP pyrophosphatase activity (75).
ALCOHOL DEHYDROGENASE (NADP+) (AK1A1) (P14550). This protein belongs to the aldo/keto reductase family and catalyses the NADPH-dependent reduction of a variety of aldehydes to their corresponding alcohols.
ALDEHYDE DEHYDROGENASE 1A3 (AL1A3) (P47895). This cytoplasmic protein belongs to the aldehyde dehydrogenase family and it is involved in the retinoic acid (RA) biosynthesis. Recognizes as substrates free retinal and cellular retinol-binding protein-bound retinal. Seems to be the key enzyme in the formation of an RA gradient along the dorso-ventral axis during the early eye development and also in the development of the olfactory system.

It is expressed at low levels in many tissues and at higher levels in salivary gland, stomach, and kidney.
ALPHA-AMYLASE 1 PRECURSOR (AMY1) (P04745). This secreted protein belongs to the glycosyl hydrolase 13 family. Its catalytic activity is the endohydrolysis of 1,4-alpha-D-glucosidic linkages in oligosaccharides and polysaccharides.
ANNEXIN A1 (ANXA1) (P04083) is a calcium/phospholipid-binding cytoplasmic protein, which promotes membrane fusion and is involved in exocytosis. This protein inhibits phospholipase A2 activity. It seems to bind from two to four calcium ions with high affinity.

This protein has been implicated in several biological processes such as cell motility, anti-apoptosis, cell surface receptor linked signal transduction, inflammatory response, cell growth and differentiation, lipid metabolic process, vesicle fusion, peptide cross-linking, and in the process of carcinogenesis (5, 36)
APOLIPOPROTEIN A-1 PRECURSOR (APOA1) (P02647) is a secreted protein that belongs to the apolipoprotein A1/A4/E family. Participates in the reverse transport of cholesterol from tissues to the liver for excretion by promoting cholesterol efflux from tissues and by acting as a cofactor for the lecithin cholesterol acyltransferase (LCAT). It is a major protein of plasma HDL, also found in chylomicrons, and is synthesized in the liver and small intestine.

Defects in APOA1 are a cause of high density lipoprotein deficiency type 2 (HDLD2), of the low HDL levels observed in high density lipoprotein deficiency type 1 (HDLD1) and of systemic non-neuropathic amyloidosis.
BETA ACTIN (ACTB) (P60709) is a cytoplasmic protein, with a molecular function of protein binding. In vertebrates 3 main groups of actin isoforms, alpha, beta and gamma have been identified. The alpha actins are found in muscle tissues and are a major constituent of the contractile apparatus. The beta and gamma actins coexist in most cell types as components of the cytoskeleton and as mediators of internal cell motility.

BETA-2-GLYCOPROTEIN 1 PRECURSOR (APOH) (P02749), also named Apolipoprotein H, is a secreted protein (expressed by the liver and secreted in plasma). It binds to various kinds of negatively charged substances such as heparin, phospholipids, and dextran sulfate. It may prevent activation of the intrinsic blood coagulation cascade by binding to phospholipids on the surface of damaged cells.

2,3-BISPHOSPHOGLYCERATE MUTASE (BPGM) (P07338) belongs to the phosphoglycerate mutase family, BPG-dependent PGAM subfamily. It is an erythroid-expressed enzyme and synthesises 2,3-bisphosphoglycerate (2,3-BPG), the allosteric modulator of haemoglobin. This ligand has a higher affinity for adult haemoglobin than for fetal haemoglobin and differential binding of it facilitates transfer of oxygen between adult and fetal blood by lowering the affinity of adult haemoglobin for oxygen (52).

CATALASE (CAT) (P04040) is an antioxidant enzyme belonging to the catalase family. It is located at the peroxisome and serves to protect cells from the toxic effects of hydrogen peroxide.

Defects in CAT are the cause of acatalasia, also known as acatalasemia. This disease is characterized by absence of catalase activity in red cells and is often associated with ulcerating oral lesions.

Oxidative stress is considered to be involved in pathogenesis of many disorders of the female genital tract (49).

CHLORIDE INTRACELLULAR CHANNEL PROTEIN 4 (CLIC4) (Q9Y696), belongs to the chloride channel CLIC family. It is a cytoplasmic protein, present in an intracellular vesicular compartment that likely represent trans-Golgi network vesicles. It is present in both soluble and membrane fractions (1, 62). Its expression is prominent in heart, placenta and skeletal muscle. It functions as a chloride channel or a regulator or accessory subunit of other proteins that could provide the pore-forming function.

It has been described to be involved in a wide variety of cellular events including regulated secretion, cell division and apoptosis (1). As it binds to various structural proteins such as tubulin or beta-actin, as well as to two 14-3-3 protein isoforms, it might be associated with cell membrane remodelling and control of cell shape (62).

Additionally, CLIC4 expression is p53, TNFalpha and c-Myc regulated. It translocates to the nucleus under conditions of cell stress, and nuclear CLIC4 is associated with cell cycle arrest and accelerated apoptosis (63, 64).

COILED-COIL DOMAIN CONTAINING PROTEIN 94 (CCDC94) (Q9BW85). There is no information regarding this protein.

CYTOSOL AMINOPEPTIDASE (AMPL) (P28838). This cytoplasmic protein is a homohexamer that belongs to the peptidase M17 family. It is presumably involved in the processing and regular turnover of intracellular proteins. Catalyzes the removal of unsubstituted N-terminal amino acids from various peptides.

F-ACTIN CAPPING PROTEIN SUBUNIT BETA (CAPZB) (P47756) binds in a Ca(2+)-independent manner to the fast growing ends of actin filaments (barbed end) thereby blocking the exchange of subunits at these ends, and stabilizing actin filaments. Unlike other capping proteins (such as gelsolin and severin), these proteins do not sever actin filaments.

Biologically, it is involved in cell motility (22, 56).

FERRITIN HEAVY CHAIN (FRIH) (P02794). This protein belongs to the ferritin family and contains 1 ferritin-like diiron domain. Stores iron in a soluble, non-toxic, readily available form and it is important for iron homeostasis. It has ferroxidase activity: iron is taken up in the ferrous form and deposited as ferric hydroxides after oxidation. The ferritin is an oligomer of 24 subunits, being two types of subunits: L (light) chain and H (heavy) chain. The major chain can be light or heavy, depending on the species and tissue type. The functional molecule forms a roughly spherical shell with a diameter of 12 nm and contains a central cavity into which the insoluble mineral iron core is deposited.

FERRITIN LIGHT CHAIN (FRIL) (P02792) contains 1 ferritin-like diiron domain and belongs to the ferritin family. Stores iron in a soluble, non-toxic, readily available form being important for iron homeostasis. Iron is taken up in the ferrous form and deposited as ferric hydroxides after oxidation. Ferritin is composed of 24 subunits of the heavy and light chains. Variation in ferritin subunit composition may affect the rates of iron uptake and release in different tissues.

Defects in this protein are the cause of hereditary hyperferritinemia-cataract syndrome (HHCS) and neuroferritinopathy, known as adult-onset basal ganglia disease.

FLAVIN REDUCTASE (BLVRB) (P30043). This cytoplasmic protein catalyzes electron transfer from reduced pyridine nucleotides to flavins as well as methylene blue, pyrroloquinoline quinone, riboflavin, or methemoglobin. It has been suggested a possible role of this protein in protecting cells from oxidative damage or in regulating iron metabolism. In the liver, converts biliverdin to bilirubin.

It is predominantly expressed in liver and erythrocytes, and at lower levels in heart, lung, adrenal gland and cerebrum.

It has been described to be overexpressed in oral squamous cell carcinoma (39).

GALECTIN-1 (LEG1) (P09382), also named beta-galactoside-binding lectin. This protein may regulate cell apoptosis and cell differentiation. It is expressed in cardiac, smooth, and skeletal muscle, neurons, thymus, kidney, placenta and hematopoietic cells. Galectin-1 can bind several glycoconjugates such as the basement membrane glycoprotein laminin, and is involved in many biological events including cell adhesion (42). It also binds beta-galactoside, CD45, CD3 and CD4. Inhibits CD45 protein phosphatase activity and therefore, the dephosphorylation of Lyn kinase.

Furthermore, it has been described a significant increase in the expression of this protein in cancer cells compared with normal adjacent endometrium (70).

GLUTATHIONE TRANSFERASE OMEGA-1 (GSTO1) (P78417). This cytoplasmic protein belongs to the GST superfamily, omega family. Exhibits glutathione-dependent thiol transferase and dehydroascorbate reductase activities, and also catalyses the reduction of monomethylarsonate, an intermediate in the pathway of arsenic biotransformation (72). It is ubiquitously expressed, with the highest expression in liver, skeletal muscle and heart, and the lowest expression in brain, placenta and lung.

GSTO1 has been linked to the age at onset of both Alzheimer's and Parkinson's diseases (72).

GLUTATHIONE S-TRANSFERASE (GSTP1) (P09211) is a cytoplasmic protein that belongs to the GST superfamily, Pi family, which are xenobiotic-detoxifying phase II enzymes catalysing the conjugation of reduced glutathione to a wide number of exogenous and endogenous hydrophobic electrophiles, including polycyclic aromatic hydrocarbons (PAH), which are widely present in the human environment and known to be carcinogenic (29).

An association between the incidence of endometriosis and the GST genotypes of patients has been suggested (28).

GLYCODELYN PRECURSOR (PAEP) (P09466), belongs to the lipocalin family and is secreted by the glandular epithelium of the endometrium upon progesterone stimulation and by the seminal vesicles (48). Quantitatively, is the main protein synthesized and secreted in the endometrium from mid-luteal phase of the menstrual cycle and during the first semester of pregnancy (71).

Depending on the site of origin, the same protein backbone is glycosylated in different ways, yielding glycodelins with different biological actions. At least two differentially glycosylated forms are found: the human endometrium-derived glycodelin-A (PAEP), with contraceptive and immunosuppressive activities, and the seminal plasma glycodelin-S, whose role is not yet known (47, 57). It has been described that PAEP immunosuppressive activity is due to its ability to induce apoptosis in activated T cells, and that the apoptotic activity requires the presence of sialic acid residues on the complex glycans (46).

In relation to endometriosis, elevated serum levels of PAEP protein has been described in patients with advanced endometriosis (32, 67), and has been suggested its role in promoting neovascularization and cell proliferation in the establishment of this disease (16).

LACTOYLGLUTATHIONE LYASE (LGUL) (Q04760). Belonging to the glyoxalase I family, this protein is involved in the glyoxal pathway catalysing the conversion of hemimercaptal, formed from methylglyoxal and glutathione, to S-lactoylglutathione.

It exists in three separable isoforms which originate from two alleles in the genome. These correspond to two homodimers and one heterodimer composed of two subunits showing different electrophoretic properties.

It has been described to be overexpressed in tumor tissues, such as ovarian and colon tumors (30, 53).

HEAT-SHOCK PROTEIN BETA 1 (HSPB1) (P04792). This protein belongs to the small heat shock protein (HSP20) family. Its localization is cytoplasmic in interphase cells, colocalizes with mitotic spindles in mitotic cells, and translocates to the nucleus during heat shock. It is involved in stress resistance (it is expressed in response to environmental stresses such as heat shock, or estrogen stimulation in MCF-7 cells) and actin organization.

Defects in HSPB1 are the cause of Charcot-Marie-Tooth disease type 2F (CMT2F), the most common inherited disorder of the peripheral nervous system, and of distal hereditary motor neuropathy (dHMN), a pure motor peripheral neuropathy without sensory abnormalities.

In adults it is found in several cell types such as breast, uterus, cervix, placenta, skin, and platelets (9).

In endometrial carcinomas, its presence is correlated with the degree of tumor differentiation. Additionally, its expression seems to be a negative prognostic factor for gastric cancer (8) and has been described to be overexpressed in oral squamous cell carcinoma (38).

HEMOGLOBIN SUBUNIT BETA (HBB) (Q9BX96). This protein present in red blood cells belongs to the globin family and it is involved in oxygen transport from the lung to the various peripheral tissues. Hemoglobin protein is a heterotetramer, consisting of two alpha and two beta chains in adult hemoglobin.

Defects in HBB are the cause of beta-thalassemia, whose hallmark is an imbalance in globin-chain production in the adult hemoglobin molecule, and of sickle cell anemia, characterized by abnormally shaped red cells resulting in chronic anemia and periodic episodes of pain, serious infections and damage to vital organs.

LEUKOCYTE ELASTASE INHIBITOR (LEI) (P30740) is a cytoplasmic protein belonging to the serpin family, Ov-serpin subfamily. It has serine-type endopeptidase inhibitor activity, regulating the activity of the neutrophil proteases elastase, cathepsin G, proteinase-3, chymase, chymotrypsin, and kallikrein-3.

MOESIN (MSN) (P26038) is a cytoplasmic protein involved in connections of major cytoskeletal structures to the plasma membrane, regulating actin cytoskeleton, control of cell shape, adhesion and motility, and modulation of signalling pathways (27, 61).

It has been described that maintains the integrity of epithelial cells antagonizing Rho small GTPase activity (26).

In *Drosophila*, cells lacking moesin lose epithelial characteristics and adopt invasive migratory behaviour (60).

PEPTIDYL-PROLYL CIS-TRANS ISOMERASE A (PPIA) (P62937), also called Cyclophilin A, is a cytoplasmic protein belonging to the cyclophilin-type PPIase family, PPIase A subfamily. Contains one PPIase cyclophilin-type domain and catalyzes the cis-trans isomerization of proline imidic peptide bonds in oligopeptides. PPIases accelerate the folding of proteins.

This protein has been reported to be overexpressed in cancer cells especially in solid tumors (7, 25).

PHOSPHOGLYCERATE MUTASE 1 (PGAM1) (P18669) is an enzyme of the glycolytic pathway that belongs to the phosphoglycerate mutase family, BPG-dependent PGAM subfamily. It is involved in the interconversion of 3- and 2-phosphoglycerate with 2,3-bisphosphoglycerate as the primer of the reaction. In mammalian tissues there are two types of phosphoglycerate mutase isozymes: type-M in muscles and type-B in other tissues, being the PGAM1 a type B protein. The Rho GTPases, Rac and Cdc42, regulate the glycolitic pathway through Paks (p21-activated kinases), which interact with PGAM1 and inactivate it (58).

PHOSPHOMEVALONATE KINASE (PMVK) (Q15126) is located in the peroxisome. Catalyzes a key step in isoprenoid/sterol biosynthesis, converting mevalonate 5-phosphate and ATP to mevalonate 5-diphosphate and ADP (24).

Despite the well documented importance of this pathway in the cause and prevention of human disease and that it is the biosynthetic root of an enormous diverse class of metabolites, the mechanism of phosphomevalonate kinase from any organism is not yet well characterized (50).

It is expressed in heart, liver, skeletal muscle, kidney, and pancreas, and at lower level in brain, placenta, and lung.

POLY(rC) BINDING PROTEIN 1 (PCBP1) (Q15365) functions as a single-stranded nucleic acid binding protein that binds preferentially to oligo dC. It may be localized both in the nucleus and cytoplasm. It is abundantly expressed in skeletal muscle, thymus and peripheral blood leucocytes while a lower expression is observed in prostate, spleen, testis, ovary, small intestine, heart, liver, adrenal and thyroid glands. The poly(C) binding proteins (PCBPs) have roles in mRNA stabilization, translational activation, and translational silencing, suggesting a complex and diverse set of post-transcriptional control pathways (41).

PYRIDOXINE-5'-PHOSPHATE OXIDASE (PNPO) (Q9NVS9). Belongs to the pyridoxamine 5'-phosphate oxidase family and oxidizes pyridoxine 5'-phosphate (PNP) and pyridoxamine 5'-phosphate (PMP) into pyridoxal 5'-phosphate (PLP), a metabolically active form of vitamin B6.

Defects in PNPO are the cause of pyridoxine-5'-phosphate oxidase deficiency (PNPO deficiency); also known as PNPO-related neonatal epileptic encephalopathy, whose main feature is the onset within hours of birth of a severe seizure disorder that does not respond to anticonvulsant drugs and can be fatal. Seizures can cease with the administration of PLP, being resistant to treatment with pyridoxine.

PROTEASOME SUBUNIT BETA TYPE 3 (PSB3) (P49720). This protein, localized in both nucleus and cytoplasm, belongs to the peptidase T1B family. The proteasome is composed of at least 15 non identical subunits which form a highly ordered ring-shaped structure. Its catalytic activity is the cleavage of peptide bonds with very broad specificity.

It has been described that PSB3 is coexpressed with the oncogene ERBB2 in 34 breast cancer biopsies, mapping within the same chromosomal location as the ERBB2 gene (15).

26S PROTEASOME NON-ATPase REGULATORY SUBUNIT 7 (PSD7) (P51665). This protein belongs to the peptidase M67A family and acts as a regulatory subunit of the 26S proteasome, which is involved in the ATP-dependent degradation of ubiquitinated proteins.

26S PROTEASOME NON-ATPase REGULATORY SUBUNIT 10 (PSD10) (O75832), also named as p28 or Gankyrin, is a component of the PA700 complex. Acts as a regulatory subunit of the 26S proteasome, which is involved in the ATP-dependent degradation of ubiquitinated proteins.

Gankyrin increases the hyperphosphorylation of Rb (retinoblastoma protein) and therefore activates E2F-dependent transcription of DNA synthesis genes. By binding to Mdm2, increases the ubiquitylation and degradation of p53 and prevents apoptosis. Therefore, it is a new oncoprotein with potent cell cycle and apoptotic properties regulator function. It is also described that is overexpressed early in hepatocarcinogenesis and in hepatocellular carcinomas (11, 40, 43).

14-3-3 PROTEIN BETA/ALPHA (1433B) (P31946). Cytoplasmic protein. Isoform alpha differs from isoform beta in being phosphorylated.

14-3-3 PROTEIN GAMMA (1433G) (P61981), also called Protein kinase C inhibitor protein 1 (KCIP-1), is a cytoplasmic protein belonging to the 14-3-3 protein family. Highly expressed in brain, skeletal muscle, and heart.

14-3-3 SIGMA (1433S) (P31947). Cytoplasmic secreted protein that has been described to be a p53-regulated inhibitor of G2/M progression.

It is present mainly in tissues enriched in stratified squamous keratinising epithelium.

14-3-3 PROTEIN THETA (1433T) (P27348) is a cytoplasmic protein belonging to the 14-3-3 protein family. It is abundantly expressed in brain, heart and pancreas, and at lower levels in kidney and placenta. Up-regulated in the lumbar spinal cord from patients with sporadic amyotrophic lateral sclerosis (ALS) compared with controls, with highest levels of expression in individuals with predominant lower motor neuron involvement.

14-3-3 PROTEIN ZETA/DELTA (1433Z) (Q6P3U9) also called Protein kinase C inhibitor protein 1, is a cytoplasmic protein belonging to the 14-3-3 protein family. Isoform delta differs from isoform zeta in being phosphorylated.

14-3-3 is a highly conserved acidic protein family, composed of seven isoforms in mammals. 14-3-3 proteins are implicated in the regulation of a large spectrum of signalling pathways, binding to a large number of partners (can interact with over 200 target proteins) usually by recognition of a phosphoserine or phosphothreonine motif, resulting in the modulation of the activity of the binding partner. The target proteins include transcription factors, biosynthetic enzymes, cytoskeletal proteins, signalling molecules, apoptosis factors and tumor suppressors.

14-3-3 proteins control progression through the cell cycle, initiation and maintenance of DNA damage checkpoints, cell growth, differentiation, survival, apoptosis, migration and spreading, activation of MAP kinases, and coordination of integrin signalling and cytoskeletal dynamics. It has been described a role of 14-3-3 proteins in human disease, particularly cancer (13, 44, 73).

Rho GDP-DISSOTIATION INHIBITOR (GDI) ALPHA, ARHGDIA (P52565) is a cytoplasmic protein that belongs to the Rho GDI family. Regulates the GDP/GTP exchange reaction of the Rho proteins (involved in cell cycle regulation) by inhibiting the dissociation of GDP from them, and the subsequent binding of GTP to them (12, 14). The GDP-bound form complexed with Rho GDI is not activated by the GDP/GTP exchange factor.

It has been described that Rho GDI directly interacts with ezrin/radixin/moesin (ERM) system, which is implicated in reorganization of actin filaments (65).

Additionally, RhoGDIalpha has been shown to be overexpressed in multiple types of tumors such as ovarian and breast cancer (54).

Rho GDP-DISSOTIATION INHIBITOR 2 (GDI5) (P52566). This cytoplasmic protein belongs to the Rho GDI family, and regulates the GDP/GTP exchange reaction of the Rho proteins by inhibiting the dissociation of GDP from them, and the subsequent binding of GTP to them. Rho proteins cycle between the GDP-bound inactive and GTP-bound active forms (receiving upstream signals through their regulators and transducing signals to downstream targets).

It is known that the Rho family mainly regulates reorganization of the actin cytoskeleton, and that the Rho GDI system plays an important role in spatial determination in the actin cytoskeletal control (55).

The Rho GDP dissotiation inhibitor 2 has been recently described to be overexpressed in oral squamous cell carcinoma (37).

RIBOSE-PHOSPHATE PYROPHOSPHOKINASE II (PRPS2) (P11908). Belongs to the ribose-phosphate pyrophosphokinase family, and catalyses the following reaction: ATP+D-ribose 5-phosphate=AMP+5-phospho-alpha-D-ribose 1-diphosphate. It is activated by magnesium and inorganic phosphate, and competitively or non-competitively inhibited by ADP, 2,3-bisphosphoglyceride or GDP.

SEPTIN-11 (SEP11) (Q9NVA2). This protein that belongs to the septin family may assemble into a multicomponent structure. Septins are a family of conserved cytoskeletal GTPases proteins involved in diverse processes including vesicle trafficking, apoptosis, remodelling of the cytoskeleton, infection, neurodegeneration, and neoplasia (20, 21).

Referring to pathological situations, a chromosomal aberration involving SEPT11 may be a cause of chronic neutrophilic leukemia. It also has been described that perturbation of septin expression is widespread in disease and tumours of various tissues (19).

SERINE/THREONINE PROTEIN KINASE Nek7 (NEK7) (Q8TDX7) is a cytoplasmic protein that belongs to the Ser/Thr protein kinase family, NIMA (never in mitosis gene a) subfamily. Contains 1 protein kinase domain.

It is highly expressed in lung, muscle, testis, brain, heart, liver, leukocyte and spleen. It has lower expression in ovary, prostate and kidney, and no expression seen in small intestine.

Members of the NIMA-related kinases (NRK) family are central regulators of various aspects of the cell cycle. Nek7 protein is enriched at the centrosome in a microtubule-independent manner and its aberrant expression results in cell morphology and mitotic progression defects (74).

SIALIC ACID SYNTHASE (SAS) (Q9NR45) is a cytoplasmic protein with N-acylneuraminate cytidylyltransferase activity and ubiquitous tissue specificity. Produces N-acetylneuraminic acid (Neu5Ac) and 2-keto-3-deoxy-D-glycero- D-galacto-nononic acid (KDN). Can also use N-acetylmannosamine 6-phosphate and mannose 6-phosphate as substrates to generate phosphorylated forms of Neu5Ac and KDN, respectively.

The sialic acids are a family of nine carbon alpha-keto acids that play a wide variety of biological roles in nature. In mammals, they are found at the distal ends of cell surface glycoconjugates, and thus are major determinants of cellular recognition and adhesion events (66).

TRANSLATIONALLY-CONTROLLED TUMOR PROTEIN (TCTP) (P13693). This cytoplasmic protein belongs to the TCTP family, and it is involved in calcium binding and microtubule stabilization. It is found in several healthy and tumoral cells including erythrocytes, hepatocytes, macrophages, platelets, keratinocytes, erythroleukemia cells, gliomas, melanomas, hepatoblastomas, and lymphomas, but it cannot be detected in kidney and renal cell carcinoma (RCC). Expressed in placenta and prostate.

This evolutionally highly conserved protein has been implicated in many cellular functions such as cell growth, cell cycle progression, malignant transformation and in the protection of cells against various stress conditions and apoptosis. In addition, an extracellular, cytokine-like function has been established for TCTP (3, 6).

TUBULIN BETA CHAIN (TBB5) (P07437). This protein belongs to the tubulin family, being the tubulin the major constituent of microtubules. Tubulin is a dimmer of alpha and beta chains, and it binds two moles of GTP, one at an exchangeable site on the beta chain and one at a non-exchangeable site on the alpha-chain.

This protein is ubiquitously expressed with highest levels in spleen, thymus and immature brain.

WD REPEAT DOMAIN 1 (WDR1) (O75083), also named Actin-interacting protein 1 (AIP1), belongs to the WD repeat AIP1 family. It is localized in the cytoplasm, in the cytoskeleton. It induces disassembly of actin filaments in conjunction with ADF/cofilin family proteins, and its deficiency results in defects in actin dynamics (34).

It has been described WDR1 overexpression as a result of staurosporin induced apoptotic cell death in human neuroblastoma derived SH-SY5Y cell line (59).

Physically and functionally interacts with caspase-11, a mammalian pro-inflamatory caspase which regulates cell migration during inflammation (34).

The current invention also provides a sensitive, efficient and rapid non-invasive in vitro method to diagnose and monitor endometriosis by using endometrial aspirates or serum as biological samples. Endometriosis can be detected by analysing the expression pattern of one or more endometriosis biomarkers in the endometrial aspirate or serum. Thus, the detection of at least one differentially expressed protein in an endometrial aspirate test sample or serum sample of a woman with endometriosis in comparison to a sample of a healthy endometrial aspirate or serum is indicative of endometriosis.

Normalization is essential to account for differences in total protein concentration and to remove bias from sample to sample. The expression levels of a control protein, whose content in endometrial sample or serum is always constant, may be used to normalize signal levels.

In an embodiment of the invention the step a) comprises measuring at least two biomarkers selected from the group as defined above.

In an embodiment of the invention the step a) comprises measuring at least three biomarkers selected from the group as defined above.

In an embodiment of the invention the step a) comprises measuring at least four biomarkers selected from the group as defined above.

In an embodiment of the invention the step a) comprises measuring 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or 51 biomarkers selected from the group as defined above.

In an embodiment of the invention the method is used to detect the presence of endometriosis and establish the diagnosis (including the stage or severity of the disease), or prognosis of endometriosis or to monitor the effect of the treatment administered to an individual suffering from this disease or to assess the lack of disease after surgical resection.

In an embodiment of the invention the sample from an individual is endometrial aspirate or serum.

In an embodiment of the invention the sample to be analysed is obtained from an individual not previously diagnosed with endometriosis.

In an embodiment of the invention the sample to be analysed is obtained from an individual who has been previously diagnosed with endometriosis.

In an embodiment of the invention the sample to be analysed is obtained from an individual receiving treatment against endometriosis.

In an embodiment of the invention the method comprises obtaining an extract of proteins from the sample.

In an embodiment of the invention the measurement of the biomarkers comprises a first step, wherein the protein extract from the sample is contacted with a composition of one or more specific antibodies, against one or more epitopes of the protein or proteins, and a second step, wherein the complexes formed by the antibodies and the proteins are quantified.

In an embodiment of the invention said antibodies are human, humanised or of non-human origin and selected from monoclonal or polyclonal antibodies, intact or recombinant fragments of antibodies, combibodies and Fab or scFv antibody fragments.

In an embodiment of the invention, for the detection or quantification of the complexes formed by antibodies and proteins, the techniques used are selected from western-blot, ELISA (Enzyme-Linked Immunosorbent assay), RIA (Radioimmunoassay), Competitive EIA (Competitive Enzyme Immunoassay), DAS-ELISA (Double Antibody Sandwich-ELISA), immunocytochemical or immunohistochemical techniques, techniques based on the use of biochips or protein microarrays that include specific antibodies, suspension antibody array technology based on microspheres and flow citometry, assays based on the precipitation of colloidal gold in formats such as dipsticks; or by affinity chromatography techniques, ligand binding assays or lectin binding assays.

In an embodiment of the invention the kit is used to detect the presence of endometriosis and establish the diagnosis (including the stage or severity of the disease), or prognosis of endometriosis or to monitor the effect of the treatment administered to an individual suffering from this disease or to assess the lack of disease after surgical resection.

For the purposes of the present invention the following definitions have been used:

The term "sets of proteins of the invention" refers to the group of proteins comprising ACTG1, SAHH, ADSS, NUDT5, AK1A1, AL1A3, AMY1, ANXA1, APOA1, ACTB, APOH, BPGM, CAT, CLIC4, CCDC94, AMPL, CAPZB, FRIH, FRIL, BLVRB, LEG1, GSTO1, GSTP1, PAEP, LGUL, HSPB1, HBB, LEI, MSN, PPIA, PGAM1, PMVK, PCBP1, PNPO, PSB3, PSD7, PSD10, 1433B, 1433G, 1433S, 1433T, 1433Z, ARHGDIA, GD15, PRPS2, SEP11, NEK7, SAS, TCTP, TBB5 and WDR1.

The term "individual" refers to all species of animals classified as mammals and includes, but is not restricted to, domestic and farm animals, primates and humans, and preferably refers to a female human of any age or race.

The term "endometriosis" refers to the disease that is typically characterised by the presence of endometrial stromal or glandular cells outside the uterine cavity.

The term "endometrial aspirate" refers to an aspirate of the endometrial fluid (not uterine washing), also referred to as an aspirate of the uterine secretion in the uterine cavity.

The term "normal sample" refers to a sample obtained from an endometriosis-free individual.

The term "differentially expressed proteins" refers to those proteins that are differentially expressed in the endometrial aspirate or serum from a patient with endometriosis and in the endometrial aspirate or serum of a woman without endometriosis. Those proteins include all the 51 biomarkers selected from the group comprising ACTG1, SAHH, ADSS, NUDT5, AK1A1, AL1A3, AMY1, ANXA1, APOA1, ACTB, APOH, BPGM, CAT, CLIC4, CCDC94, AMPL, CAPZB, FRIH, FRIL, BLVRB, LEG1, GSTO1, GSTP1, PAEP, LGUL, HSPB1, HBB, LEI, MSN, PPIA, PGAM1, PMVK, PCBP1, PNPO, PSB3, PSD7, PSD10, 1433B, 1433G, 1433S, 1433T, 1433Z, ARHGDIA, GD15, PRPS2, SEP11, NEK7, SAS, TCTP, TBB5 and WDR1, as well as any protein of an endometrial aspirate or serum sample, whose quantification is altered when comparing two different endometrial aspirate or serum samples, one from a healthy individual and one from a patient with endometriosis. The term "differentially expressed protein" may refer both to an overexpressed protein or a repressed protein.

The term "endometriosis biomarker" relates to each of the "differentially expressed proteins" in the endometrial aspirate or serum from a patient with endometriosis and in the endometrial aspirate or serum of a woman without endometriosis, whose presence/absence and/or quantification can distinguish between endometriosis and non-endometriosis patients.

The term "constantly expressed proteins" refers to those proteins that are equally expressed in the endometrial aspirate or serum from an endometriosis patient and in the endometrial aspirate or serum from a non-endometriosis control.

The term "inversely expressed" refers to two differentially expressed proteins whose expression patterns are opposite (that is, in a sample one is overexpressed while the other is repressed or viceversa).

The term "endometriosis stage I" refers to an individual who is suffering from minimal endometriosis according to the American Society for Reproductive Medicine classification (ASRM)

The term "endometriosis stage 11" refers to an individual who is suffering from mild endometriosis according to the American Society for Reproductive Medicine classification (ASRM)

The term "endometriosis stage III" refers to an individual who is suffering from moderate endometriosis according to the American Society for Reproductive Medicine classification (ASRM)

The term "endometriosis stage 1V" refers to an individual who is suffering from severe endometriosis according to the American Society for Reproductive Medicine classification (ASRM)

The term "treatment" refers to any process, action, application or the like, wherein an individual is subject to medical aid with the object of improving his condition, directly or indirectly.

The term "surgery" refers to the process of removing the endometriotic lesions.

The term "diagnosis" of endometriosis relates to the process of identifying or determining the nature and stage of endometriosis through evaluation of one or more endometriosis biomarkers.

The term "specificity" refers to the ability of a test to exclude the presence of a disease when it is truly not present. Specificity is the proportion of non-diseased patients for whom there is a correct negative test, expressed as the number of true negatives divided by the sum of true negatives and false positives.

The term "sensitivity" refers to the ability of a test to detect a disease when it is truly present. Sensitivity is the proportion of all diseased patients for whom there is a positive test, determined as the number of the true positives divided by the sum of true positives and false negatives.

The term "gene" refers to a region of a molecular chain of deoxyribonucleotides that encodes a protein and may represent a portion of a coding sequence or a complete coding sequence.

The term "protein" refers to at least one molecular chain of amino acids linked intermolecularly through either covalent or non-covalent bonds. The term includes all forms of post-translational protein modifications, for example glycosylation, phosphorylation or acetylation.

The terms "peptide" and "polypeptide" refer to molecular chains of amino acids that represent a protein fragment. The terms "protein" and "peptide" are used indistinguishably.

The term "antibody" refers to a Y-shaped protein (known as immunoglobulin) on the surface of B cells that is secreted into the blood or lymph in response to an antigenic stimulus, such as an exogenous protein, bacterium, virus, parasite, or transplanted organ, and that exhibits a specific binding activity for a target molecule called an "antigen". The antigen binding region of immunoglobulins can be divided into either $F(ab')_2$ or Fab fragments. The term "antibody" includes monoclonal and polyclonal antibodies, either intact or fragments derived from them; and includes human antibodies, humanised antibodies and antibodies of non-human origin. A "non-human antibody" is an antibody generated by an animal species other than *Homo sapiens*. A "humanized antibody" is a genetically engineered antibody wherein the minimal mouse part from a murine antibody is fused to a human antibody. Generally, humanized antibodies are 5-10% mouse and 90-95% human. A "human antibody" is an antibody derived from transgenic mice carrying human antibody genes or from human cells. The "monoclonal antibodies" are homogeneous, highly specific antibody populations directed against a single antigenic site or "determinant" of the target molecule. "Polyclonal antibodies" include heterogeneous antibody populations that are directed against different antigenic determinants of the target molecule.

The term "specific antibody" refers to an antibody generated against a specific protein (in this case against a particular endometriosis marker).

The term "complex formed by the antibodies" refers to a complex formed by an antigen and its specific antibody.

The term "combibody" (combinatorial antibody) refers to an antibody displayed on filamentous phages, which allows direct screening of cDNA libraries for expression of cellsurface-reactive antibodies, without the need for antibody production and purification using bacteria or eukaryotic cell systems.

The term "Fab recombinant antibody" refers to a recombinant antibody that only contains the Fab fragment that is univalent and useful when the antibody has a very high avidity for its antigen. They can be recombinantly obtained if the protein sequence is known.

The term "ScFv antibody fragment" refers to a single chain variable fragment (scFv) that can be expressed in bacterial cultures.

The term "epitope" refers to an antigenic determinant of a protein, which is the sequence of amino acids of the protein that a specific antibody recognises. Such epitopes may be comprised of a contiguous stretch of amino acids (linear epitope) or of non-contiguous amino acids that are brought into proximity with one another by virtue of the three dimensional folding of the polypeptide chain (discontinuous epitopes).

The term "solid phase", as it is used in the present invention refers to a non-aqueous matrix to which the antibody can bind. Examples of materials for the solid phase include but are not limited to glass, polysaccharides (for example agarose), polyacrylamide, polystyrene, polyvinylic alcohol and silicons. Examples of solid phase forms are the well of a plate or a purification column.

The term "dipstick" refers to a device dipped into a liquid to perform some kind of test that might be of quantity or of the chemical properties of the liquid. This kind of dipstick is usually made of paper or cardboard and is impregnated with reagents whose colour changes indicate some feature of the liquid.

The term "carrier" refers to a mechanism or device by which something is conveyed or conducted.

The term "packaging" refers to the containment and packing prior to sale with the primary purpose of facilitating the purchase and use of a product.

The term "biochip" refers to a collection of miniaturized test sites (microarrays) arranged on a solid substrate that permits many tests to be performed at the same time in order to achieve higher throughput and speed.

An embodiment of the invention relates to a non-invasive in vitro method that comprises the quantification of one or more ratios between two different proteins selected from these sets of proteins of the invention in an endometrial aspirate or serum from an individual.

Another embodiment relates to a non-invasive in vitro method that comprises the quantification of one or more ratios between two different proteins selected from these sets of proteins of the invention in an endometrial aspirate or serum sample from an individual, wherein the two different proteins are inversely expressed.

In another embodiment the stage of development of the endometriosis disease is determined by quantitative determination of one or more proteins selected from these sets of proteins of the invention either alone or in combination in the same sample.

In another embodiment the method allows to determine the progression of the disease when the same protein is compared from different samples obtained at different times.

In another embodiment one or more proteins selected from these sets of proteins of the invention may be used to monitor the efficacy of other pharmacological or surgical treatment.

In another embodiment the detection and/or quantification of one or more of the protein or proteins comprises a first step, wherein the protein extract of the sample is placed in contact with a composition of one or more specific antibodies, against one or more epitopes of the protein or proteins, and a second step, wherein the complexes formed by the antibodies and the proteins are quantified.

In another embodiment the specific antibodies used for the detection of one or more proteins selected from these sets of proteins of the invention are human, humanised or of non-human origin and selected from monoclonal or polyclonal antibodies, intact or recombinant fragments of antibodies, combibodies and Fab or scFv antibody fragments.

In another embodiment the techniques used for the detection and/or quantification of the complexes formed by antibodies and proteins, the techniques used are selected from the group comprised by: western-blot, ELISA (Enzyme-Linked Immunosorbent assay), RIA (Radioimmunoassay), Competitive EIA (Competitive Enzyme Immunoassay), DAS-ELISA (Double Antibody Sandwich-ELISA), immunocytochemical or immunohistochemical techniques, techniques based on the use of biochips or protein microarrays that include specific antibodies, suspension antibody array technology based on microspheres and flow citometry, assays based on the precipitation of colloidal gold in formats such as dipsticks; or by affinity chromatography techniques, ligand binding assays or lectin binding assays.

Another embodiment relates to the use of one or more sequences derived from one or more proteins selected from these sets of proteins of the invention to detect the presence of endometriosis and establish the diagnosis (including the stage), and/or prognosis of endometriosis and/or to monitor the effect of the treatment administered to an individual suffering from this disease and/or to assess the lack of disease after surgical resection.

Another embodiment relates to the use of one or more nucleotides or peptide sequences derived from one or more proteins selected from the sets of proteins of the invention, alone or in any combination, in methods to screen for, identify, develop and evaluate the efficiency of other compounds to endometriosis, wherein the proteins are present in endometrial aspirate or serum.

Another embodiment relates to a kit to perform a method as previously defined comprising any combination of antibodies that specifically recognises one or more of these proteins and a carrier in suitable packaging, the kit being employed to detect the presence of endometriosis and establish the diagnosis (including the stage), and/or prognosis of endometriosis and/or to monitor the effect of the treatment administered to an individual suffering from this disease and/or to assess the lack of disease after surgical resection.

There is a wide range of immunological assays available to detect and/or quantify the formation of specific antigen-antibody complexes; numerous competitive or non-competitive protein-binding assays have been described previously and a large number of these are commercially available. Hence, one or more proteins selected from the sets of proteins of the invention can be quantified with antibodies such as, for example: monoclonal antibodies, polyclonal antibodies, either intact or recombinant fragments of these, combibodies and Fab or scFv fragments of antibodies, specific for one or more proteins selected from the sets of proteins of the invention; these antibodies are human, humanised or of animal origin. The antibodies used in these assays can be labelled or unlabelled; the antibodies can be used in a wide range of assays. Marker molecules that can be used to label antibodies include radionuclides, enzymes, fluorophores, chemoluminescent reagents, enzymatic substrates or cofactors, enzymatic inhibitors, particles, colorants and derivatives. The higher the antibody binding specificity is, the lower the antigen concentration that can be detected.

There are a wide variety of assays well known to those skilled in the art that can be used in the present invention, which use unlabelled antibodies (primary antibody) and labelled antibodies (secondary antibodies); these techniques include but are not limited to the western-blot or western transfer, ELISA (Enzyme-Linked immunosorbent assay), RIA (Radioimmunoassay), Competitive EIA (Competitive enzyme immunoassay), DAS-ELISA (Double antibody sandwich-ELISA), immunocytochemical and immunohistochemical techniques, techniques based on the use of biochips or protein microarrays that include specific antibodies, suspension antibody array technology based on microspheres and flow citometry or colloidal precipitation in formats such as dipsticks. Other ways to detect and/or quantify one or more proteins selected from the sets of proteins of the invention include affinity chromatography techniques, ligand binding assays or lectin binding assays. The preferred embodiments of this aspect of the invention are protein microarrays, suspension antibody arrays and double antibody sandwich ELISA (DAS-ELISA). In these immunoassays any antibody, or combination of antibodies can be used, that are specific against one or more epitopes of the sets of proteins of the invention. As an example of one of the many possible formats of this assay, a monoclonal or polyclonal antibody, or a fragment of this antibody, or a combination of these antibodies that recognise one or more epitopes of the sets of proteins of the invention are attached to the surface of a solid phase support and placed in contact with the sample to be analysed and incubated for a specific time and in appropriate conditions to form the antigen-antibody complexes. After washing in appropriate conditions to eliminate non-specific complexes, an indicator reagent, consisting in a monoclonal or polyclonal antibody, or a fragment of this antibody, or a combination of these and which recognises one or more epitopes of the sets of proteins of the invention, bound to a signal generating molecule, is incubated with the antigen-antibody complexes in appropriate conditions of time and temperature. The presence of the selected one or more proteins selected from the sets of proteins of the invention in the sample to be analysed is detected and, if present, quantified and the signal generated is measured. The amount of one or more proteins selected from the sets of proteins of the invention present in the sample to be analysed is proportional to these signals.

As indicated above, the method of the invention involves monitoring the stage of endometriosis by quantitating the differentially expressed soluble proteins within an endometrial aspirate or serum sample through specific antibodies. As will be appreciated by those skilled in the art, any means for specifically identifying and quantifying these proteins are contemplated.

In the following description, the method used to obtain and analyse the total protein content of human endometrial aspirate samples is disclosed. The method involves the sample collection and processing, the use of 2D electrophoresis to separate proteins within the sample, the image analysis of the proteomes obtained from each sample to compare the proteins that are present, statistical analysis of the expression levels of the proteins of the samples, identification of the differentially expressed proteins (statistically significant proteins) and the use of one or more of the differentially expressed proteins of the invention to generate protein-specific antibodies to be used as endometriosis markers. Those biomarker validation methods and the final development of a kit for a non-invasive diagnostic of endometriosis will also be described.

The comparative proteome analysis was performed between endometrial aspirate samples obtained from healthy individuals (controls) and patients diagnosed with endometriosis (I: minimal, II: mild, III: moderate, IV: severe) in an attempt to identify differentially expressed proteins in the various stages of endometriosis (healthy vs endometriosis I-II vs endometriosis III-IV). The proteins that showed differential expression were identified by peptide mass fingerprinting using mass spectrometry and database search.

The present invention will be further illustrated by data obtained from the experiments. These examples are given by way of illustration only and are not to be construed as limiting.

DESCRIPTION OF THE METHODOLOGY USED

To identify differentially expressed proteins in endometriosis disease, protein profiles of women diagnosed with endometriosis were compared to protein profiles of women with a non-endometriosis diagnostic using proteomic approaches.

Population Studied

The sample used in this invention refers to an aspirate of the endometrial fluid (not uterine washing), also referred to as an aspirate of the uterine secretion in the uterine cavity, of women who have been diagnosed with endometriosis, as well as the aspirate obtained from healthy women.

In order to include samples in the study, some inclusion and exclusion criteria have been established:

Patients
Inclusion Criteria:
1. Women aged 18 to 45
2. Patients surgically diagnosed by laparoscopy
3. Stage I-IV endometriosis
4. Regular cycles (24-35 days)
5. Sample collection on the secretory phase (LH+4/+12)
6. Signed consent Exclusion Criteria:
1. Other gynecologic pathologies (ovarian or endometrial cancer, hydrosalpinx, etc. . . . )
2. Hormonal treatment during the previous 3 months to sample collection Controls
Inclusion Criteria:
1. Women aged 18 to 45
2. Patients surgically diagnosed by laparoscopy
3. No surgical evidence of endometriosis
4. Regular cycles (24-35 days)
5. Sample collection on the secretory phase (LH+4/+12)
6. Signed consent Exclusion Criteria:
1. Other gynecologic pathologies (ovarian, or endometrial cancer, hydrosalpinx, etc. . . . )
2. Hormonal treatment during the previous 3 months to sample collection Samples of those women were obtained from Spanish Health Network hospitals and Fertility centres, and are classified as follows (Table 1):

TABLE 1

Classification of the samples used in the image analysis.

| | Number of images obtained |
|---|---|
| Healthy control | 32 |
| Endometriosis I | 9 |

TABLE 1-continued

Classification of the samples used in the image analysis.

| | Number of images obtained |
|---|---|
| Endometriosis II | 5 |
| Endometriosis III | 13 |
| Endometriosis IV | 19 |
| Total | 78 |

Endometriosis stages I and II were grouped, as well as endometriosis stages III and IV, having a total of three groups to compare: 32 healthy controls vs 14 endometriosis I-II vs 32 endometriosis III-IV.

Sample Collection

Samples were collected during the post-ovulatory secretory phase of the menstrual cycle (from day LH+4 to LH+12) due to the higher amount of protein present in this phase, and estrogen dependence of the disease. In order to collect the endometrial fluid, a 2-3 mm diameter flexible cannula connected to a 20 ml syringe was introduced into the uterine cavity and vacuum was applied with the syringe. Aspirates were expelled into standard 2 ml cryogenic tubes and immediately frozen at −80° C. or liquid nitrogen. Typical aspirate volumes vary from 5 to 100 μl.

The samples were very heterogenic, ranging from white-transparent viscous secretion to red ones with blood clumps or containing endometrial tissue.

Protein Extraction

First, samples must be resuspended in 500 ul of PBS and purified using the Vivapure Anti-HAS/IgG Kit (Vivascience AG, Hannover, Germany) to remove albumin (specially if the sample is contaminated with blood) and class G immunoglobulins. After this step, samples were precipitated with 15% w/v trichloroacetic acid during one hour at 4° C., followed by centrifugation (10 min, 16000×g, 4° C.). Pellets were washed with 1 ml of prechilled acetone and centrifuged. After drying the pellets at room temperature for 20 min, they were rehydrated with 470 ul of rehydration solution containing urea 7 M, thiourea 2 M and CHAPS 2%. Protein content of the resuspended samples was determined by Bradford assay using Bio-Rad Protein Assay (Bio-Rad) following the manufacturer's instructions.

To perform the two dimension (2DE) electrophoresis, 200 ug of each sample were taken and DeStreak Rehydration solution 1.2% (Ref. 17-6003-18, GE Healthcare, Little Chalfont, UK), bromophenol blue 0.002% and IPG buffer pH 3-10 NL 0.5% (Ref. 17-6000-88, GE Healthcare) added to a final volume of 450 ul of rehydration solution. Each sample was loaded into immobilized pH gradients, Inmobiline™ DryStrip (24 cm strips, pH 3-10 NL) (Ref. 17-6002-45, GE Healthcare) and first dimension (IEF, isoelectric focusing) was applied in an Ettan™ IPGphor™ 3 Isoelectric Focusing System (GE Healthcare) following manufacturer's instructions to resolve proteins by their charge (isoelectric point) in a pH range of 3-10. The voltage applied was as follows: active rehydration of the strips at 50 V for 11 hours, 250 V for 15 minutes, increasing voltage to 10.000 V by maintaining the intensity to a 50 μA per strip as maximum, finishing the IEF when the voltage reached >90.000 Vht.

Next, the strips were equilibrated and the second dimension (SDS-PAGE) performed to separate proteins in acrylamide gels according to their molecular weight. For this purpose, 12.5% acrylamide gels (dimensions: 26×20 cm) were polymerised in the lab using the Ettan DALT twelve Gel Caster from GE Healthcare. Strips were hold on top of the gels and were run in the Ettan DALT twelve Large Format Vertical System following manufacturer's instructions until the electrophoresis front reached the bottom of the gels. Then, gels were stained using silver nitrate (Silver Staining Kit, ref 17-1150-01, GE Healthcare), and scanned (ImageScanner Umax VII, GE Healthcare) for subsequent image analysis of the protein spots, air-dried and stored at room temperature. For some samples more than one 2D-gel had been run.

A typical 2D image gel obtained from an endometrial aspirate sample is shown as a representative example in FIG. 1.

Analysis of the Protein Spots on the Gels

Figure 2:
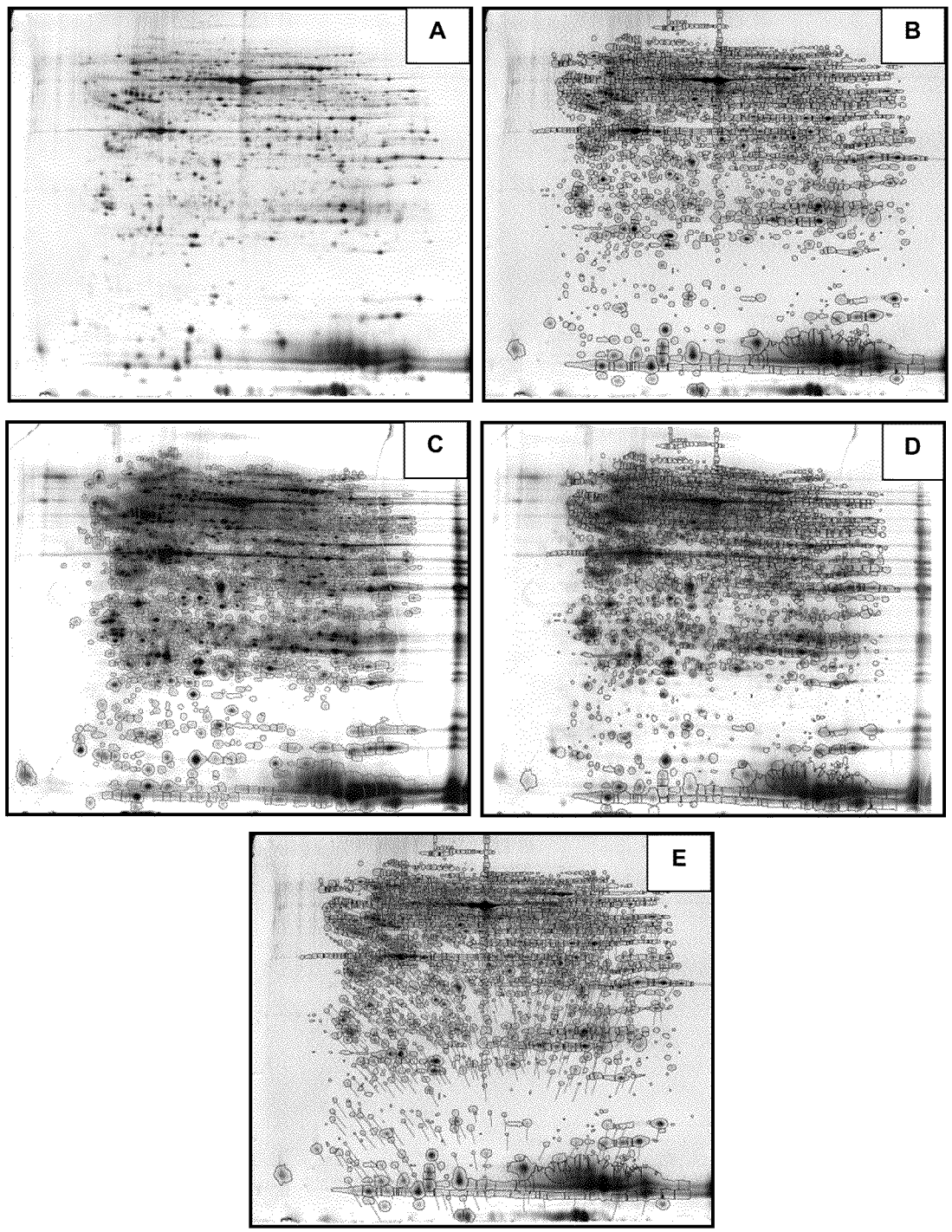
FIG. 2 shows the endometrial aspirate sample image analysis stages. A, 2D image of one endometrial aspirate sample gel; B, spots detected in A image; C, spots detected in the reference gel; D, A image warping illustration (automatic process that corrects the differences between gels as a consequence of the experimental procedure); E, manual matching illustration between A image and the reference gel C (link between as much as possible spots in each gel to the same spots present in the reference gel).

Progenesis™ 2D Evolution software, version 2004, from Nonlinear Dynamics (UK) was used to analyse scanned image files in a 300 dpi (dot per inch) format and 8 bits/channel. The Progenesis240 software (Nonlinear Dynamics) transforms the data of the flat image into a 3D image, where the intensity of each spot is represented by a peak volume that correlates with the relative amount of the corresponding protein in the endometrial aspirate of the patient. The image analysis was performed in a semiautomatic manner with the following steps, which are illustrated in FIG. 2:

spot detection and quantitation in all gels.

warping and matching of all gels over a reference gel (a selected gel that ideally includes all the spots present in an endometrial aspirate sample).

background subtraction (mode of non-spot).

normalization of the volume values of each spot by the total spot volume.

Data matrix corresponding to each spot expression was exported for subsequent statistical analysis.

Statistical Analysis

Statistical analysis was done by using SPSS software. Non-parametric K independent samples test was performed by applying Kruskal Wallis test, and statistical differences ($p<0.05$) were detected between controls vs endometriosis I-II vs endometriosis III-IV. The fold change (FC) of the expression level of each protein between the different groups studied was obtained comparing the median of the expression intensity values obtained from the Progenesis software.

The differential spots were checked on the 2D images to exclude matching failures and when necessary the matching was corrected and the statistical analysis was performed again.

Protein Identification

The identification of the differential spots was carried out by mass spectrometry. Those endometrial aspirate samples whose 2D electrophoresis had shown statistically significant spots were submitted again to preparative 2D electrophoresis and the spots excised from the gel. Proteins were digested with trypsin and the resulting peptides were applied to a mass spectrometer (MALDI-ToF, Matrix-Assisted Laser-Desorption/Ionization Time Of Flight). Peptide fingerprints were generated and peptide sequence determined. These fingerprints were matched into a Mascot database.

Table 2 shows the list of statistically significant differential spots (with its 'p' value) and corresponding proteins identified by mass spectrometry. Each spot number is represented along with the corresponding protein symbol and Uniprot code. The fold change of the expression level of each protein between the different groups studied is also included. Spots with FC values higher than 1 are overexpressed, whereas spots lower than 1 are down-regulated.

TABLE 2

Statistically significant differential spot identification in endometriosis.

| Spot | Name | Symbol | Uniprot | p | FC endo I-II vs control | FC endo III-IV vs control | FC endo III-IV vs I-II |
|------|------|--------|---------|---|---------|---------|---------|
| 73400 | Annexin A1 | ANXA1 | P04083 | 0.015 | 0.70 | 1.52 | 2.17 |
| 72989 | Adenosylhomocysteinase | SAHH | P23526 | 0.051 | 0.81 | 1.33 | 1.64 |
| 72989 | Actin, cytoplasmic 2 | ACTG1 | P63261 | 0.051 | 0.81 | 1.33 | 1.64 |
| 75266 | Glutathione S-transferase | GSTP1 | P09211 | 0.039 | 1.23 | 1.35 | 1.10 |
| 74204 | Ferritin light chain | FRIL | P02792 | 0.019 | 2.08 | 1.50 | 0.72 |
| 75241 | 14-3-3 protein zeta/delta | 1433Z | Q6P3U9 | 0.008 | 1.56 | 1.31 | 0.83 |
| 75242 | 14-3-3 protein beta/alpha | 1433B | P31946 | 0.030 | 1.44 | 1.27 | 0.88 |
| 73152 | Leukocyte elastase inhibitor | LEI | P30740 | 0.037 | 0.57 | 0.71 | 1.25 |
| 73299 | Sialic acid synthase | SAS | Q9NR45 | 0.012 | 0.90 | 1.98 | 2.19 |
| 74452 | Peptidyl-prolyl cis-trans isomerase A | PPIA | P62937 | 0.019 | 1.71 | 1.63 | 0.95 |
| 75183 | 14-3-3 protein theta | 1433T | P27348 | 0.027 | 1.66 | 1.67 | 1.01 |
| 73769 | 14-3-3 protein sigma | 1433S | P31947 | 0.007 | 2.34 | 1.48 | 0.63 |
| 72500 | Catalase | CAT | P04040 | 0.050 | 0.69 | 1.01 | 1.47 |
| 74460 | Peptidyl-prolyl cis-trans isomerase A | PPIA | P62937 | 0.011 | 1.50 | 1.62 | 1.08 |
| 75182 | 14-3-3 protein gamma | 1433G | P61981 | 0.009 | 6.08 | 2.06 | 0.34 |
| 73992 | Proteasome subunit beta type 3 | PSB3 | P49720 | 0.013 | 1.23 | 1.90 | 1.55 |
| 74001 | Translationally-controled tumor protein | TCTP | P13693 | 0.035 | 1.36 | 1.81 | 1.33 |
| 72359 | WD repeat protein 1 | WDR1 | O75083 | 0.033 | 0.73 | 1.61 | 2.22 |
| 72162 | Moesin | MSN | P26038 | 0.014 | 0.63 | 1.23 | 1.97 |
| 72143 | Moesin | MSN | P26038 | 0.001 | 0.47 | 1.00 | 2.11 |
| 74052 | Flavin reductase | BLVRB | P30043 | 0.025 | 1.94 | 0.96 | 0.49 |
| 74002 | Lactoylglutathione lyase | LGUL | Q04760 | 0.004 | 1.80 | 2.16 | 1.20 |
| 73892 | Rho GDP-dissotiation inhibitor 2 | GD15 | P52566 | 0.004 | 0.47 | 1.54 | 3.26 |
| 73892 | Heat-shock protein beta 1 | HSPB1 | P04792 | 0.004 | 0.47 | 1.54 | 3.26 |
| 73892 | Glycodelin precursor | PAEP | P09466 | 0.004 | 0.47 | 1.54 | 3.26 |
| 74126 | Ferritin heavy chain | FRIH | P02794 | 0.001 | 3.29 | 1.69 | 0.51 |
| 73580 | Ribose-phosphate pyrophosphokinase II | PRPS2 | P11908 | 0.029 | 0.34 | 1.78 | 5.30 |
| 73812 | Poly(rC)-binding protein 1 | PCBP1 | Q15365 | 0.004 | 2.61 | 1.00 | 0.38 |
| 73983 | 26S proteasome non-ATPase regulatory subunit 10 | PSD10 | O75832 | 0.007 | 2.82 | 1.69 | 0.60 |
| 73782 | No ID | | | 0.026 | 1.48 | 1.45 | 0.98 |
| 73085 | Beta-actin | ACTB | P07437 | 0.020 | 1.28 | 0.74 | 0.58 |
| 72640 | Tubulin beta chain | TBB5 | P07437 | 0.006 | 2.17 | 1.23 | 0.57 |
| 73884 | Rho GDP-dissotiation inhibitor 1 | RhoGDI1 | P52565 | 0.011 | 1.73 | 2.37 | 1.37 |
| 73927 | Apolipoprotein A-1 precursor | APOA1 | P02647 | 0.030 | 1.69 | 1.42 | 0.84 |
| 73309 | Beta-actin | ATCB | P60709 | 0.025 | 0.73 | 2.06 | 2.82 |
| 74127 | Phosphomevalonate kinase | PMVK | Q15126 | 0.036 | 1.94 | 2.47 | 1.27 |
| 73814 | Bisphosphoglycerate mutase | BPGM | P07738 | 0.007 | 1.93 | 1.09 | 0.56 |
| 75164 | Coiled-coil domain containing protein 94 | CCDC94 | Q9BW85 | 0.021 | 1.77 | 4.05 | 2.29 |
| 73678 | F-actin capping protein subunit beta | CAPZB | P47756 | 0.037 | 0.33 | 0.75 | 2.23 |
| 74617 | Hemoglobin subunit beta | HBB | Q9BX96 | 0.031 | 1.85 | 1.55 | 0.83 |
| 74617 | Galectin-1 | LEG1 | P09382 | 0.031 | 1.85 | 1.55 | 0.83 |
| 72814 | Septin-11 | SEP11 | Q9NVA2 | 0.035 | 0.64 | 1.53 | 2.40 |
| 72814 | Cytosol aminopeptidase | AMPL | P28838 | 0.035 | 0.64 | 1.53 | 2.40 |
| 75213 | Beta-2-glycoprotein 1 precursor | APOH | P02749 | 0.003 | 0.33 | 0.47 | 1.44 |
| 75213 | Alpha-amylase 1 precursor | AMY1 | P04745 | 0.003 | 0.33 | 0.47 | 1.44 |
| 73748 | Serine/threonine-protein kinase Nek7 | NEK7 | Q8TDX7 | 0.001 | 1.30 | 2.48 | 1.91 |
| 73774 | Chloride intracellular channel protein 4 | CLIC4 | Q9Y696 | 0.020 | 1.61 | 1.28 | 0.80 |
| 73749 | Glutathione transferase omega-1 | GSTO1 | P78417 | 0.011 | 2.50 | 1.29 | 0.52 |
| 72991 | Adenylosuccinate synthetase isozyme 2 | ADSS | P30520 | 0.005 | 0.86 | 1.92 | 2.24 |
| 73871 | Phosphoglycerate mutase I | PGAM1 | P18669 | 0.045 | 1.31 | 1.40 | 1.06 |
| 73862 | Pyridoxine-5'-phosphate oxidase | PNPO | Q9NVS9 | 0.024 | 2.12 | 1.53 | 0.72 |
| 74129 | Ferritin heavy chain | FRIH | P02794 | 0.014 | 2.95 | 2.30 | 0.78 |
| 74068 | No ID | | | 0.045 | 1.39 | 1.56 | 1.12 |
| 73362 | 26S proteasome non-ATPase regulatory subunit 7 | PSD7 | P51665 | 0.024 | 3.73 | 1.82 | 0.49 |
| 73362 | Alcohol dehydrogenase [NADP+] | AK1A1 | P14550 | 0.024 | 3.73 | 1.82 | 0.49 |
| 73756 | No ID | | | 0.015 | 1.71 | 1.54 | 0.90 |
| 72803 | No ID | | | 0.015 | 0.48 | 2.00 | 4.18 |
| 73651 | ADP-sugar pyrophosphatase | NUDT5 | Q9UKK9 | 0.047 | 0.31 | 0.79 | 2.57 |
| 73651 | Actin, cytoplasmic 2 | ACTG1 | P63261 | 0.047 | 0.31 | 0.79 | 2.57 |
| 72621 | Aldehyde dehydrogenase 1A3 | AL1A3 | P47895 | 0.002 | 0.21 | 0.68 | 3.23 |

Validation of the Biomarkers

Monoclonal and/or polyclonal antibodies (either commercially purchased or generated following immunization protocols) will be tested for reactivity and sensitivity to detect the biomarkers in endometrial aspirate and serum samples, using ELISA type immunoassays and 1D and 2D western-blot methods.

Recombinant proteins will be also purchased or specifically made to set up the detection of the biomarkers. For the production of recombinant proteins, available cDNAs (tagged cDNA) of the protein of interest will be purchased and expressed in *E. coli*. The expressed protein will be purified according to the tag nature and run on a SDS-PAGE gel.

For the generation of antibodies against recombinant proteins, the purified proteins will be used to immunize rabbits for polyclonal or mice for monoclonal antibodies. Antibodies will be raised using standard methodologies; immunizing animals with the protein of interest diluted in Freund's complete adjuvant (Gibco, Grand Island, N.Y.) first, and then every month during three months with the protein in incomplete adjuvant. Rabbit or mice sera (prior to fusion, in this case) will be used as polyclonal antisera to show if they are reactive to the protein preparations by standard western blot technique.

For western blotting experiments, protein samples (20 µg of total protein) are mixed with SDS-PAGE gel loading buffer supplemented with 5% beta-mercaptoethanol and incubated at 100° C. for 5 min, before being loaded on polyacrylamide gels. Following electrophoresis, proteins are transferred to nitrocellulose membranes. Duplicate gels are run and blotted, so one membrane is proved with antibodies raised against one or more of the selected sets of proteins of the invention, while the second membrane is proved with an antibody raised against actin (GE Healthcare) or other normalizing protein as a control for protein loading. Finally, membranes are hybridised with a secondary antibody conjugated with peroxidase (GE Healthcare) and the chemoluminescent signal is detected using the ECL system (GE Healthcare) with high performance chemiluminescence film (Hyperfilm ECL, GE Healthcare).

For the ELISA detection method, the following protocol will be applied: antibodies are passively attached overnight at 4° C. to solid phase (96-well plates) by incubation in a carbonate buffer pH 9.6. Free antibodies are washed away with PBST-BSA 3% and the plate is blocked for 1 hour at room temperature in PBST-BSA 3%. Next, the endometrial aspirate sample is added in the same buffer and incubated for 1 h at room temperature. After some washes with PBST to remove the unbound antigen (biomarker), biotin-conjugated antibodies are added in PBST-BSA 3% buffer and incubated for 1 h at room temperature. After washing with PBST to remove the unbound labelled antibodies, streptavidin-HRP (Horseradish Peroxidase) complexes are added to bind to the sandwich (in PBST-BSA 3% buffer). After washing with PBST, a colorimetric substrate called TMB (SIGMA, T4319) is added and the reaction is stopped (Stop Solution from SIGMA, S5689) when colour develops. This colour is quantified in a spectrometer. Experiment conditions, such as incubation times and solution dilutions are optimised for each particular case. Antibodies are recommended to be against different regions of the antigen and are also previously checked by western-blot analysis to ensure their specificity. In this sense, it is also recommended the use of monoclonal antibodies.

Development of an In Vitro Non-Invasive Method for Endometriosis Diagnostic

A specific immunoassay will be developed to the simultaneous detection of the selected biomarkers included in this invention. The assay will consist in capturing the biomarker with a bait antibody and once bound, it will be detected by using detection antibodies labelled with biotin in order to bind later streptavidin-fluorophore complexes. Depending on the number of biomarkers to be detected, the kit will be a conventional ELISA assay (if only one marker is included) or a protein chip or suspension antibody array (if a panel of biomarkers is included). The detection will be based on the fluorescent or colorimetric signal generated, which will be proportional to the amount of target (biomarker) bound. The final detection system will determine the levels of the biomarkers included in the invention along with a normalization protein, a protein whose levels do not change significantly among patients. All the antibodies included in the assay will be monoclonal antibodies due to their specificity and the reproducibility in the production step.

In case of developing a protein chip, the protocol, with limited modifications, will be as follows: Slides are prepared using a spotter (Microgrid II 610, Biorobotics) in a multiplex format that allows the simultaneous analysis of 16 samples (Nexterion MPX16, Schott). Each well of the spotted slide is incubated for 15 min at room temperature with 100 ul of working buffer PBST-FCS 3% (PBS 1X+TWEEN 20 0.2%+FCS 3%) for the blocking step. The solution is removed and the incubation repeated for 45 min at room temperature. If a spiked control is used in the assay, it must be added to each endometrial aspirate sample at a predetermined optimal concentration. Then, 40 ul of the samples diluted 1:1 in PBST-FCS 3% (with the spiked control loaded) are incubated in the wells for 90 min at room temperature on a shaker (75 rpm). After 3 washes of 5 min each with 100 ul of PBST-FCS 3% per well, the biotin-labeled antibody pool is added (40 ul/well) and incubated for 1 h at room temperature on a shaker (75 rpm). This pool contains the detection antibodies for the biomarkers and also one directed against the spiked control. After 3 washes of 5 min each with 100 ul of PBST-FCS 3% per well, the developing step is performed adding 40 ul of streptavidin-Cy3 diluted 1:100 in PBST-FCS 3%. The following steps must be performed in darkness due to the fluorophore presence. After 45 min incubation, the wells are washed twice (5 min each) with 100 ul of PBST-FCS 3% and twice with 100 ul of PBS 1X. Then the slide is washed twice (15 s each) manually in a recipient containing H2O MΩ. Finally the slide is dried by centrifugation at 500 rpm during 5 min.

After the described incubation steps of the samples, antibodies, etc., slides are scanned at 560 nm (Axon Scanner GenePix 4100) and fluorescence values of fluorophore are quantitated and normalized using the spiked control protein. Finally, a multivariate analysis is performed for data analysis (SPSS software). Predictive models (algorithms) are generated to discriminate patients from controls, and for each model the sensitivity and specificity is determined.

In case of using a suspension antibody array technology, it will be based on microspheres and flow citometry. This technology uses color-coded beads (internally dyed with red and infrared fluorophores), called microspheres, into distinct sets. Each bead set can be coated with an antibody specific to a particular marker, allowing the capture of specific analytes from a sample and its subsequent detection with other specific marked (biotinylated) antibody.

This technique includes a reader that detects individual beads by flow cytometry. The optics assembly consists of two lasers: one laser excites the dye mixture inside the microspheres and the second laser excites the fluorophore bound to the surface of the microspheres. Photo diode detectors measure the excitation emission intensities of the color coding classification dye mixtures inside the microspheres, and a photomultiplier tube detects the excitation emission intensity of the reporter molecule bound to the surface of the microspheres.

Results of the analyses are processed and provided in a report format.

This technology allows multiplexing unique assays within a single sample.

REFERENCE LIST

1. Ashley, R. H. 2003. Challenging accepted ion channel biology: p64 and the CLIC family of putative intracellular anion channel proteins (Review). Mol. Membr. Biol. 20:1-11.
2. Bergqvist, A. 1992. Extragenital endometriosis. A review. Eur. J. Surg. 158:7-12.
3. Bommer, U. A. and B. J. Thiele. 2004. The translationally controlled tumour protein (TCTP). Int. J. Biochem. Cell Biol. 36:379-385.
4. Bryan, K. E., K. K. Wen, M. Zhu, N. D. Rendtorff, M. Feldkamp, L. Tranebjaerg, K. H. Friderici, and P. A. Rubenstein. 2006. Effects of human deafness gamma-actin mutations (DFNA20/26) on actin function. J. Biol. Chem. 281:20129-20139.
5. Buckingham, J. C., C. D. John, E. Solito, T. Tierney, R. J. Flower, H. Christian, and J. Morris. 2006. Annexin 1, glucocorticoids, and the neuroendocrine-immune interface. Ann. N.Y. Acad. Sci. 1088:396-409.
6. Chen, S. H., P. S. Wu, C. H. Chou, Y. T. Yan, H. Liu, S. Y. Weng, and H. F. Yang-Yen. 2007. A knockout mouse approach reveals that TCTP functions as an essential factor for cell proliferation and survival in a tissue- or cell type-specific manner. Mol. Biol. Cell 18:2525-2532.
7. Choi, K. J., Y. J. Piao, M. J. Lim, J. H. Kim, J. Ha, W. Choe, and S. S. Kim. 2007. Overexpressed cyclophilin A in cancer cells renders resistance to hypoxia- and cisplatin-induced cell death. Cancer Res. 67:3654-3662.
8. Ciocca, D. R., S. Oesterreich, G. C. Chamness, W. L. McGuire, and S. A. Fuqua. 1993. Biological and clinical implications of heat shock protein 27,000 (Hsp27): a review. J. Natl. Cancer Inst. 85:1558-1570.
9. Ciocca, D. R., S. Oesterreich, G. C. Chamness, W. L. McGuire, and S. A. Fuqua. 1993. Biological and clinical implications of heat shock protein 27,000 (Hsp27): a review. J. Natl. Cancer Inst. 85:1558-1570.
10. Datta, S. K., O. M. Guicherit, and R. E. Kellems. 1994. Adenylosuccinate synthetase: a dominant amplifiable genetic marker in mammalian cells. Somat. Cell Mol. Genet. 20:381-389.
11. Dawson, S., H. Higashitsuji, A. J. Wilkinson, J. Fujita, and R. J. Mayer. 2006. Gankyrin: a new oncoprotein and regulator of pRb and p53. Trends Cell Biol. 16:229-233.
12. DerMardirossian, C. and G. M. Bokoch. 2005. GDIs: central regulatory molecules in Rho GTPase activation. Trends Cell Biol. 15:356-363.
13. Dougherty, M. K. and D. K. Morrison. 2004. Unlocking the code of 14-3-3. J. Cell Sci. 117:1875-1884.
14. Dransart, E., B. Olofsson, and J. Cherfils. 2005. RhoGDIs revisited: novel roles in Rho regulation. Traffic. 6:957-966.
15. Dressman, M. A., A. Baras, R. Malinowski, L. B. Alvis, I. Kwon, T. M. Walz, and M. H. Polymeropoulos. 2003. Gene expression profiling detects gene amplification and differentiates tumor types in breast cancer. Cancer Res. 63:2194-2199.
16. Esfandiari, N., J. Ai, Z. Nazemian, M. H. Javed, L. Gotlieb, and R. F. Casper. 2007. Expression of glycodelin and cyclooxygenase-2 in human endometrial tissue following three-dimensional culture. Am. J. Reprod. Immunol. 57:49-54.
17. Garry, R. 2006. Diagnosis of endometriosis and pelvic pain. Fertil. Steril. 86:1307-1309.
18. Gupta, S., A. Agarwal, L. Sekhon, N. Krajcir, M. Cocuzza, and T. Falcone. 2006. Serum and peritoneal abnormalities in endometriosis: potential use as diagnostic markers. Minerva Ginecol. 58:527-551.
19. Hall, P. A., K. Jung, K. J. Hillan, and S. E. Russell. 2005. Expression profiling the human septin gene family. J. Pathol. 206:269-278.
20. Hall, P. A., K. Jung, K. J. Hillan, and S. E. Russell. 2005. Expression profiling the human septin gene family. J. Pathol. 206:269-278.
21. Hanai, N., K. Nagata, A. Kawajiri, T. Shiromizu, N. Saitoh, Y. Hasegawa, S. Murakami, and M. Inagaki. 2004. Biochemical and cell biological characterization of a mammalian septin, Sept11. FEBS Lett. 568:83-88.
22. Hart, M. C. and J. A. Cooper. 1999. Vertebrate isoforms of actin capping protein beta have distinct functions In vivo. J. Cell Biol. 147:1287-1298.
23. Hearns-Stokes, R., C. Mayers, C. Zahn, D. Cruess, J. A. Gustafsson, J. Segars, and L. Nieman. 2006. Expression of the proto-oncoprotein breast cancer nuclear receptor auxiliary factor (Brx) is altered in eutopic endometrium of women with endometriosis. Fertil. Steril. 85:63-70.
24. Herdendorf, T. J. and H. M. Miziorko. 2006. Phosphomevalonate kinase: functional investigation of the recombinant human enzyme. Biochemistry 45:3235-3242.
25. Howard, B. A., R. Furumai, M. J. Campa, Z. N. Rabbani, Z. Vujaskovic, X. F. Wang, and E. F. Patz, Jr. 2005. Stable RNA interference-mediated suppression of cyclophilin A diminishes non-small-cell lung tumor growth in vivo. Cancer Res. 65:8853-8860.
26. Hughes, S. C. and R. G. Fehon. 2007. Understanding ERM proteins—the awesome power of genetics finally brought to bear. Curr. Opin. Cell Biol. 19:51-56.
27. Hughes, S. C. and R. G. Fehon. 2007. Understanding ERM proteins—the awesome power of genetics finally brought to bear. Curr. Opin. Cell Biol. 19:51-56.
28. Hur, S. E., J. Y. Lee, H. S. Moon, and H. W. Chung. 2005. Polymorphisms of the genes encoding the GSTM1, GSTT1 and GSTP1 in Korean women: no association with endometriosis. Mol. Hum. Reprod. 11:15-19.
29. Hur, S. E., J. Y. Lee, H. S. Moon, and H. W. Chung. 2005. Polymorphisms of the genes encoding the GSTM1, GSTT1 and GSTP1 in Korean women: no association with endometriosis. Mol. Hum. Reprod. 11:15-19.
30. Jones, M. B., H. Krutzsch, H. Shu, Y. Zhao, L. A. Liotta, E. C. Kohn, and E. F. Petricoin, III. 2002. Proteomic analysis and identification of new biomarkers and therapeutic targets for invasive ovarian cancer. Proteomics. 2:76-84.
31. Koninckx, P. R., C. Meuleman, S. Demeyere, E. Lesaffre, and F. J. Cornillie. 1991. Suggestive evidence that pelvic endometriosis is a progressive disease, whereas deeply infiltrating endometriosis is associated with pelvic pain. Fertil. Steril. 55:759-765.
32. Koninckx, P. R., L. Riittinen, M. Seppala, and F. J. Cornillie. 1992. CA-125 and placental protein 14 concentrations in plasma and peritoneal fluid of women with deeply infiltrating pelvic endometriosis. Fertil. Steril. 57:523-530.

33. Kyama, C. M., D. T'jampens, A. Mihalyi, P. Simsa, S. Debrock, E. Waelkens, B. Landuyt, C. Meuleman, V. Fulop, J. M. Mwenda, and T. M. D'Hooghe. 2006. Protein-Chip technology is a useful method in the pathogenesis and diagnosis of endometriosis: a preliminary study. Fertil. Steril.
34. Li, J., W. M. Brieher, M. L. Scimone, S. J. Kang, H. Zhu, H. Yin, U. H. von Andrian, T. Mitchison, and J. Yuan. 2007. Caspase-11 regulates cell migration by promoting Aip1-Cofilin-mediated actin depolymerization. Nat. Cell Biol. 9:276-286.
35. Li, X., Z. Zhu, D. Mo, H. Wang, S. Yang, S. Zhao, and K. Li. 2007Comparative molecular characterization of ADSS1 and ADSS2 genes in pig (*Sus scrofa*). Comp Biochem. Physiol B Biochem. Mol. Biol. 147:271-277.
36. Lim, L. H. and S. Pervaiz. 2007. Annexin 1: the new face of an old molecule. FASEB J. 21:968-975.
37. Lo, W. Y., M. H. Tsai, Y. Tsai, C. H. Hua, F. J. Tsai, S. Y. Huang, C. H. Tsai, and C. C. Lai. 2007. Identification of over-expressed proteins in oral squamous cell carcinoma (OSCC) patients by clinical proteomic analysis. Clin. Chim. Acta 376:101-107.
38. Lo, W. Y., M. H. Tsai, Y. Tsai, C. H. Hua, F. J. Tsai, S. Y. Huang, C. H. Tsai, and C. C. Lai. 2007. Identification of over-expressed proteins in oral squamous cell carcinoma (OSCC) patients by clinical proteomic analysis. Clin. Chim. Acta 376:101-107.
39. Lo, W. Y., M. H. Tsai, Y. Tsai, C. H. Hua, F. J. Tsai, S. Y. Huang, C. H. Tsai, and C. C. Lai. 2007. Identification of over-expressed proteins in oral squamous cell carcinoma (OSCC) patients by clinical proteomic analysis. Clin. Chim. Acta 376:101-107.
40. Lozano, G. and G. P. Zambetti. 2005. Gankyrin: an intriguing name for a novel regulator of p53 and RB. Cancer Cell 8:3-4.
41. Makeyev, A. V. and S. A. Liebhaber. 2002. The poly(C)-binding proteins: a multiplicity of functions and a search for mechanisms. RNA. 8:265-278.
42. Maquoi, E., F. A. van den Brule, V. Castronovo, and J. M. Foidart. 1997. Changes in the distribution pattern of galectin-1 and galectin-3 in human placenta correlates with the differentiation pathways of trophoblasts. Placenta 18:433-439.
43. Mayer, R. J. and J. Fujita. 2006. Gankyrin, the 26 S proteasome, the cell cycle and cancer. Biochem. Soc. Trans. 34:746-748.
44. Mhawech, P. 2005. 14-3-3 proteins—an update. Cell Res. 15:228-236.
45. Morell, R. J., K. H. Friderici, S. Wei, J. L. Elfenbein, T. B. Friedman, and R. A. Fisher. 2000. A new locus for late-onset, progressive, hereditary hearing loss DFNA20 maps to 17q25. Genomics 63:1-6.
46. Mukhopadhyay, D., S. SundarRaj, A. Alok, and A. A. Karande. 2004. Glycodelin A, not glycodelin S, is apoptotically active. Relevance of sialic acid modification. J. Biol. Chem. 279:8577-8584.
47. Mukhopadhyay, D., S. SundarRaj, A. Alok, and A. A. Karande. 2004. Glycodelin A, not glycodelin S, is apoptotically active. Relevance of sialic acid modification. J. Biol. Chem. 279:8577-8584.
48. Mukhopadhyay, D., S. SundarRaj, A. Alok, and A. A. Karande. 2004. Glycodelin A, not glycodelin S, is apoptotically active. Relevance of sialic acid modification. J. Biol. Chem. 279:8577-8584.
49. Pejic, S., J. Kasapovic, A. Todorovic, V. Stojiljkovic, and S. B. Pajovic. 2006. Lipid peroxidation and antioxidant status in blood of patients with uterine myoma, endometrial polypus, hyperplastic and malignant endometrium. Biol. Res. 39:619-629.
50. Pilloff, D., K. Dabovic, M. J. Romanowski, J. B. Bonanno, M. Doherty, S. K. Burley, and T. S. Leyh. 2003. The kinetic mechanism of phosphomevalonate kinase. J. Biol. Chem. 278:4510-4515.
51. Poliness, A. E., M. G. Healey, S. P. Brennecke, and E. K. Moses. 2004. Proteomic approaches in endometriosis research. Proteomics. 4:1897-1902.
52. Pritlove, D. C., M. Gu, C. A. Boyd, H. S. Randeva, and M. Vatish. 2006. Novel placental expression of 2,3-bisphosphoglycerate mutase. Placenta 27:924-927.
53. Ranganathan, S. and K. D. Tew. 1993. Analysis of glyoxalase-I from normal and tumor tissue from human colon. Biochim. Biophys. Acta 1182:311-316.
54. Reimer, J., S. Bien, J. Sonnemann, J. F. Beck, T. Wieland, H. K. Kroemer, and C. A. Ritter. 2007. Reduced expression of Rho guanine nucleotide dissociation inhibitor-alpha modulates the cytotoxic effect of busulfan in HEK293 cells. Anticancer Drugs 18:333-340.
55. Sasaki, T. and Y. Takai. 1998. The Rho small G protein family-Rho GDI system as a temporal and spatial determinant for cytoskeletal control. Biochem. Biophys. Res. Commun. 245:641-645.
56. Schafer, D. A., Y. O. Korshunova, T. A. Schroer, and J. A. Cooper. 1994. Differential localization and sequence analysis of capping protein beta-subunit isoforms of vertebrates. J. Cell Biol. 127:453-465.
57. Seppala, M., H. Bohn, and Y. Tatarinov. 1998. Glycodelins. Tumour. Biol. 19:213-220.
58. Shalom-Barak, T. and U. G. Knaus. 2002. A p21-activated kinase-controlled metabolic switch up-regulates phagocyte NADPH oxidase. J. Biol. Chem. 277:40659-40665.
59. Short, D. M., I. D. Heron, J. L. Birse-Archbold, L. E. Kerr, J. Sharkey, and J. McCulloch. 2007. Apoptosis induced by staurosporine alters chaperone and endoplasmic reticulum proteins: Identification by quantitative proteomics. Proteomics. 7:3085-3096.
60. Speck, O., S. C. Hughes, N. K. Noren, R. M. Kulikauskas, and R. G. Fehon. 2003. Moesin functions antagonistically to the Rho pathway to maintain epithelial integrity. Nature 421:83-87.
61. Speck, O., S. C. Hughes, N. K. Noren, R. M. Kulikauskas, and R. G. Fehon. 2003. Moesin functions antagonistically to the Rho pathway to maintain epithelial integrity. Nature 421:83-87.
62. Suginta, W., N. Karoulias, A. Aitken, and R. H. Ashley. 2001. Chloride intracellular channel protein CLIC4 (p64H1) binds directly to brain dynamin I in a complex containing actin, tubulin and 14-3-3 isoforms. Biochem. J. 359:55-64.
63. Suh, K. S., M. Malik, A. Shukla, and S. H. Yuspa. 2007. CLIC4, skin homeostasis and cutaneous cancer: surprising connections. Mol. Carcinog. 46:599-604.
64. Suh, K. S., M. Mutoh, M. Gerdes, and S. H. Yuspa. 2005. CLIC4, an intracellular chloride channel protein, is a novel molecular target for cancer therapy. J. Investig. Dermatol. Symp. Proc. 10:105-109.
65. Takahashi, K., T. Sasaki, A. Mammoto, K. Takaishi, T. Kameyama, S. Tsukita, and Y. Takai. 1997. Direct interaction of the Rho GDP dissociation inhibitor with ezrin/radixin/moesin initiates the activation of the Rho small G protein. J. Biol. Chem. 272:23371-23375.
66. Tanner, M. E. 2005. The enzymes of sialic acid biosynthesis. Bioorg. Chem. 33:216-228.

67. Telimaa, S., A. Kauppila, L. Ronnberg, A. M. Suikkari, and M. Seppala. 1989. Elevated serum levels of endometrial secretory protein PP14 in patients with advanced endometriosis. Suppression by treatment with danazol and high-dose medroxyprogesterone acetate. Am. J. Obstet. Gynecol. 161:866-871.
68. Turner, M. A., X. Yang, D. Yin, K. Kuczera, R. T. Borchardt, and P. L. Howell. 2000. Structure and function of S-adenosylhomocysteine hydrolase. Cell Biochem. Biophys. 33:101-125.
69. Ulukus, M., H. Cakmak, and A. Arici. 2006. The role of endometrium in endometriosis. J. Soc. Gynecol. Investig. 13:467-476.
70. van den Brule, F. A., C. Buicu, A. Berchuck, R. C. Bast, M. Deprez, F. T. Liu, D. N. Cooper, C. Pieters, M. E. Sobel, and V. Castronovo. 1996. Expression of the 67-kD laminin receptor, galectin-1, and galectin-3 in advanced human uterine adenocarcinoma. Hum. Pathol. 27:1185-1191.
71. Waites, G. T., S. C. Bell, R. A. Walker, and P. L. Wood. 1990. Immunohistological distribution of the secretory endometrial protein, 'pregnancy-associated endometrial alpha 2-globulin', a glycosylated beta-lactoglobulin homologue, in the human fetus and adult employing monoclonal antibodies. Hum. Reprod. 5:487-493.
72. Whitbread, A. K., A. Masoumi, N. Tetlow, E. Schmuck, M. Coggan, and P. G. Board. 2005. Characterization of the omega class of glutathione transferases. Methods Enzymol. 401:78-99.
73. Wilker, E. and M. B. Yaffe. 2004. 14-3-3 Proteins—a focus on cancer and human disease. J. Mol. Cell Cardiol. 37:633-642.
74. Yissachar, N., H. Salem, T. Tennenbaum, and B. Motro. 2006. Nek7 kinase is enriched at the centrosome, and is required for proper spindle assembly and mitotic progression. FEBS Lett. 580:6489-6495.
75. Yu, H. N., E. K. Song, S. M. Yoo, Y. R. Lee, M. K. Han, C. Y. Yim, J. Y. Kwak, and J. S. Kim. 2007. Activation of NUDT5, an ADP-ribose pyrophosphatase, by nitric oxide-mediated ADP-ribosylation. Biochem. Biophys. Res. Commun. 354:764-768.
76. Yu, H. N., E. K. Song, S. M. Yoo, Y. R. Lee, M. K. Han, C. Y. Yim, J. Y. Kwak, and J. S. Kim. 2007. Activation of NUDT5, an ADP-ribose pyrophosphatase, by nitric oxide-mediated ADP-ribosylation. Biochem. Biophys. Res. Commun. 354:764-768.
77. Zhang, H., Y. Niu, J. Feng, H. Guo, X. Ye, and H. Cui. 2006. Use of proteomic analysis of endometriosis to identify different protein expression in patients with endometriosis versus normal controls. Fertil. Steril.
78. Zhu, M., T. Yang, S. Wei, A. T. DeWan, R. J. Morell, J. L. Elfenbein, R. A. Fisher, S. M. Leal, R. J. Smith, and K. H. Friderici. 2003. Mutations in the gamma-actin gene (ACTG1) are associated with dominant progressive deafness (DFNA20/26). Am. J. Hum. Genet. 73:1082-1091.

The invention claimed is:

1. A non-invasive in vitro method comprising a) measuring one or more biomarkers selected from the group of Actin cytoplasmic 2, Adenosylhomocysteinase, Adenylosuccinate synthetase isozyme 2, ADP-sugar pyrophosphatase, Alcohol dehydrogenase [NADP+], Aldehyde dehydrogenase 1A3, Alpha-amylase 1 precursor, Annexin A1, Apolipoprotein A-1 precursor, Beta-actin, Beta-2-glycoprotein 1 precursor, Bisphosphoglycerate mutase, Catalase, Chloride intracellular channel protein 4, Coiled-coil domain containing protein 94, Cytosol aminopeptidase, F-actin capping protein subunit beta, Ferritin heavy chain, Ferritin light chain, Flavin reductase, Galectin-1, Glutathione transferase omega-1, Glutathione S-transferase, Glycodelin precursor, Lactoylglutathione lyase, Heat-shock protein beta 1, Hemoglobin subunit beta, Leukocyte elastase inhibitor, Moesin, Peptidyl-prolyl cis-trans isomerase A, Phosphoglycerate mutase I, Phosphomevalonate kinase, Poly(rC)-binding protein 1, Pyridoxine-5'-phosphate oxidase, Proteasome subunit beta type 3, 26S proteasome non-ATPase regulatory subunit 7, 26S proteasome non-ATPase regulatory subunit 10, 14-3-3 protein beta/alpha, 14-3-3 protein gamma, 14-3-3 protein sigma, 14-3-3 protein theta, 14-3-3 protein zeta/delta, Rho GDP-dissotiation inhibitor 1, Rho GDP-dissotiation inhibitor 2, Ribose-phosphate pyrophosphokinase II, Septin-11, Serine/threonine-protein kinase Nek7, Sialic acid synthase, Translationally-controlled tumor protein, Tubulin beta chain and WD repeat protein 1 in a sample from an individual, and b) comparing the measurements of the one or more biomarkers in the sample with the measurement of the one or more biomarkers in a normal sample, wherein an alteration in the measurement of the one or more biomarkers compared to the measurement of the one or more biomarkers in the normal sample is indicative of endometriosis.

2. The method according to claim 1, wherein the step a) comprises measuring at least two biomarkers selected from the group consisting of Actin cytoplasmic 2, Adenosylhomocysteinase, Adenylosuccinate synthetase isozyme 2, ADP-sugar pyrophosphatase, Alcohol dehydrogenase [NADP+], Aldehyde dehydrogenase 1A3, Alpha-amylase 1 precursor, Annexin A1, Apolipoprotein A-1 precursor, Beta-actin, Beta-2-glycoprotein 1 precursor, Bisphosphoglycerate mutase, Catalase, Chloride intracellular channel protein 4, Coiled-coil domain containing protein 94, Cytosol aminopeptidase, F-actin capping protein subunit beta, Ferritin heavy chain, Ferritin light chain, Flavin reductase, Galectin-1, Glutathione transferase omega-1, Glutathione S-transferase, Glycodelin precursor, Lactoylglutathione lyase, Heat-shock protein beta 1, Hemoglobin subunit beta, Leukocyte elastase inhibitor, Moesin, Peptidyl-prolyl cis-trans isomerase A, Phosphoglycerate mutase I, Phosphomevalonate kinase, Poly(rC)-binding protein 1, Pyridoxine-5'-phosphate oxidase, Proteasome subunit beta type 3, 26S proteasome non-ATPase regulatory subunit 7, 26S proteasome non-ATPase regulatory subunit 10, 14-3-3 protein beta/alpha, 14-3-3 protein gamma, 14-3-3 protein sigma, 14-3-3 protein theta, 14-3-3 protein zeta/delta, Rho GDP-dissotiation inhibitor 1, Rho GDP-dissotiation inhibitor 2, Ribose-phosphate pyrophosphokinase II, Septin-11, Serine/threonine-protein kinase Nek7, Sialic acid synthase, Translationally-controlled tumor protein, Tubulin beta chain and WD repeat protein 1 and combinations thereof.

3. The method according to claim 1, wherein the step a) comprises measuring at least three biomarkers selected from the group consisting of Actin cytoplasmic 2, Adenosylhomocysteinase, Adenylosuccinate synthetase isozyme 2, ADP-sugar pyrophosphatase, Alcohol dehydrogenase [NADP+], Aldehyde dehydrogenase 1A3, Alpha-amylase 1 precursor, Annexin A1, Apolipoprotein A-1 precursor, Beta-actin, Beta-2-glycoprotein 1 precursor, Bisphosphoglycerate mutase, Catalase, Chloride intracellular channel protein 4, Coiled-coil domain containing protein 94, Cytosol aminopeptidase, F-actin capping protein subunit beta, Ferritin heavy chain, Ferritin light chain, Flavin reductase, Galectin-1, Glutathione transferase omega-1, Glutathione S-transferase, Glycodelin precursor, Lactoylglutathione lyase, Heat-shock protein beta 1, Hemoglobin subunit beta, Leukocyte elastase inhibitor, Moesin, Peptidyl-prolyl cis-trans isomerase A, Phosphoglycerate mutase I, Phosphomevalonate kinase, Poly(rC)-binding protein 1, Pyridoxine-5'-phosphate oxidase, Proteasome subunit beta type 3, 26S proteasome non-ATPase regulatory subunit 7, 26S proteasome non-ATPase regulatory subunit 10, 14-3-3 protein beta/alpha, 14-3-3 protein gamma, 14-3-3 protein sigma, 14-3-3 protein theta, 14-3-3 protein zeta/delta, Rho GDP-dissotiation inhibitor 1, Rho GDP-dissotiation inhibitor 2, Ribose-phosphate pyrophosphokinase II, Septin-11, Serine/threonine-protein kinase Nek7, Sialic acid synthase, Translationally-controlled tumor protein, Tubulin beta chain and WD repeat protein 1 and combinations thereof.

4. The method according to claim 1, wherein the step a) comprises measuring at least four biomarkers selected from the group consisting of Actin cytoplasmic 2, Adenosylhomocysteinase, Adenylosuccinate synthetase isozyme 2, ADP-sugar pyrophosphatase, Alcohol dehydrogenase [NADP+], Aldehyde dehydrogenase 1A3, Alpha-amylase 1 precursor, Annexin A1, Apolipoprotein A-1 precursor, Beta-actin, Beta-2-glycoprotein 1 precursor, Bisphosphoglycerate mutase, Catalase, Chloride intracellular channel protein 4, Coiled-coil domain containing protein 94, Cytosol aminopeptidase, F-actin capping protein subunit beta, Ferritin heavy chain, Ferritin light chain, Flavin reductase, Galectin-1, Glutathione transferase omega-1, Glutathione S-transferase, Glycodelin precursor, Lactoylglutathione lyase, Heat-shock protein beta 1, Hemoglobin subunit beta, Leukocyte elastase inhibitor, Moesin, Peptidyl-prolyl cis-trans isomerase A, Phosphoglycerate mutase I, Phosphomevalonate kinase, Poly(rC)-binding protein 1, Pyridoxine-5'-phosphate oxidase, Proteasome subunit beta type 3, 26S proteasome non-ATPase regulatory subunit 7, 26S proteasome non-ATPase regulatory subunit 10, 14-3-3 protein beta/alpha, 14-3-3 protein gamma, 14-3-3 protein sigma, 14-3-3 protein theta, 14-3-3 protein zeta/delta, Rho GDP-dissotiation inhibitor 1, Rho GDP-dissotiation inhibitor 2, Ribose-phosphate pyrophosphokinase II, Septin-11, Serine/threonine-protein kinase Nek7, Sialic acid synthase, Translationally-controlled tumor protein, Tubulin beta chain and WD repeat protein 1 and combinations thereof.

5. The method according to claim 1, wherein the step a) comprises measuring 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or 51 biomarkers selected from the group consisting of Actin cytoplasmic 2, Adenosylhomocysteinase, Adenylosuccinate synthetase isozyme 2, ADP-sugar pyrophosphatase, Alcohol dehydrogenase [NADP+], Aldehyde dehydrogenase 1A3, Alpha-amylase 1 precursor, Annexin A1, Apolipoprotein A-1 precursor, Beta-actin, Beta-2-glycoprotein 1 precursor, Bisphosphoglycerate mutase, Catalase, Chloride intracellular channel protein 4, Coiled-coil domain containing protein 94, Cytosol aminopeptidase, F-actin capping protein subunit beta, Ferritin heavy chain, Ferritin light chain, Flavin reductase, Galectin-1, Glutathione transferase omega-1, Glutathione 5-transferase, Glycodelin precursor, Lactoylglutathione lyase, Heat-shock protein beta 1, Hemoglobin subunit beta, Leukocyte elastase inhibitor, Moesin, Peptidyl-prolyl cis-trans isomerase A, Phosphoglycerate mutase I, Phosphomevalonate kinase, Poly(rC)-binding protein 1, Pyridoxine-5'-phosphate oxidase, Proteasome subunit beta type 3, 26S proteasome non-ATPase regulatory subunit 7, 26S proteasome non-ATPase regulatory subunit 10, 14-3-3 protein beta/alpha, 14-3-3 protein gamma, 14-3-3 protein sigma, 14-3-3 protein theta, 14-3-3 protein zeta/delta, Rho GDP-dissotiation inhibitor 1, Rho GDP-dissotiation inhibitor 2, Ribose-phosphate pyrophosphokinase II, Septin-11, Serine/threonine-protein kinase Nek7, Sialic acid synthase, Translationally-controlled tumor protein, Tubulin beta chain and WD repeat protein 1 and combinations thereof.

6. The method according to claim 1 which is used to detect the presence of endometriosis and establish the diagnosis including the stage or severity of the disease, or prognosis of endometriosis or to monitor the effect of the treatment administered to an individual suffering from this disease or to assess the lack of disease after surgical resection.

7. The method according to claim 1 wherein the sample from an individual is endometrial aspirate or serum.

8. The method according to claim 1 wherein the sample to be analyzed is obtained from an individual not previously diagnosed with endometriosis.

9. The method according to claim 1 wherein the sample to be analyzed is obtained from an individual who has been previously diagnosed with endometriosis.

10. The method according to claim 1 wherein the sample to be analyzed is obtained from an individual receiving treatment against endometriosis.

11. The method according to claim 1 comprising obtaining an extract of proteins from the sample.

12. The method according to claim 11 wherein the detection and quantification of the biomarkers comprises a first step, wherein the protein extract from the sample is contacted with a composition of one or more specific antibodies, against one or more epitopes of the protein or proteins, and a second step, wherein the complexes formed by the antibodies and the proteins are quantified.

13. The method according to claim 11, wherein said antibodies are human, humanized or of non-human origin and selected from the group consisting of monoclonal antibodies, polyclonal antibodies, intact fragments of antibodies, recombinant fragments of antibodies, combibodies, and Fab antibody fragments, and scFv antibody fragments.

14. The method according to claim 11 or 12 wherein for the detection or quantification of the complexes formed by antibodies and proteins, the techniques used are selected from the group consisting of western-blot, ELISA (Enzyme-Linked Immunosorbent assay), RIA (Radioimmunoassay), Competitive EIA (Competitive Enzyme Immunoassay), DAS-ELISA (Double Antibody Sandwich-ELISA), immunocytochemical techniques, immunohistochemical techniques, techniques based on the use of biochips that include specific antibodies, techniques based on the use of protein microarrays that include specific antibodies, suspension antibody array technology based on microspheres and flow citometry, assays based on the precipitation of colloidal gold affinity chromatography techniques, ligand binding assays, and lectin binding assays.

* * * * *

UNITED STATES PATENT AND TRADEMARK OFFICE
CERTIFICATE OF CORRECTION

PATENT NO. : 8,679,769 B2  Page 1 of 1
APPLICATION NO. : 12/811159
DATED : March 25, 2014
INVENTOR(S) : Daniel Nagore et al.

It is certified that error appears in the above-identified patent and that said Letters Patent is hereby corrected as shown below:

On the Title Page, Item (73) Assignee: change "Proteomike, S.L." to --Proteomika, S.L.--

In the Claims, Column 31, Line 51: change "tathione 5-transferase, Glycodelin precursor, Lactoylglu-" to --tathione S-transferase, Glycodelin precursor, Lactoylglu- --

Signed and Sealed this
Fifth Day of August, 2014

Michelle K. Lee
*Deputy Director of the United States Patent and Trademark Office*